United States Patent [19]
Abidin et al.

[11] Patent Number: 5,250,063
[45] Date of Patent: Oct. 5, 1993

[54] SURGICAL SCALPEL WITH RETRACTABLE GUARD

[75] Inventors: Michael R. Abidin; Steven P. Lehmbeck, both of Baltimore, Md.

[73] Assignee: Leonard Bloom, Towson, Md.; a part interest

[21] Appl. No.: 825,556

[22] Filed: Jan. 24, 1992

[51] Int. Cl.$^5$ ............................................. A61B 17/32
[52] U.S. Cl. ...................................... 606/167; 30/151; 30/335
[58] Field of Search ............... 606/166, 167, 172, 181, 606/182, 185; 30/162, 151, 164, 167, 286, 335; 128/751

[56] References Cited

U.S. PATENT DOCUMENTS

| | | | |
|---|---|---|---|
| 1,914,153 | 6/1933 | Ogden | 30/339 |
| 2,885,780 | 5/1959 | Campbell | 30/162 |
| 3,906,626 | 9/1975 | Riuli | 30/162 |
| 4,491,132 | 1/1985 | Aikins | 606/167 |
| 5,071,426 | 12/1991 | Dolgin et al. | 606/167 |

FOREIGN PATENT DOCUMENTS

3722899  1/1989  Fed. Rep. of Germany ...... 606/167

*Primary Examiner*—C. Fred Rosenbaum
*Assistant Examiner*—W. Lewis
*Attorney, Agent, or Firm*—Leonard Bloom

[57] ABSTRACT

A surgical scalpel is provided with a retractable guard for its cutting blade. The scalpel includes a resiliently-biased locking means and a releasing mechanism for, alternatively, selectively locking the guard in an extended position for covering the blade and in a retracted position for exposing the blade. The guard is disposed on the body of the scalpel for sliding movement between its extended and retracted positions—with the use of only one hand—and without requiring the surgeon, nurse and/or assistant to take his or her eyes away from the patient. The locking mechanism produces a auditory sensory warning to signal to the user thereof that the guard is locked into either its extended or retracted position, without the necessity of visually observing the scalpel, and the locking and releasing mechanisms may be tactually located by the user and activated without visually observing the scalpel.

29 Claims, 11 Drawing Sheets

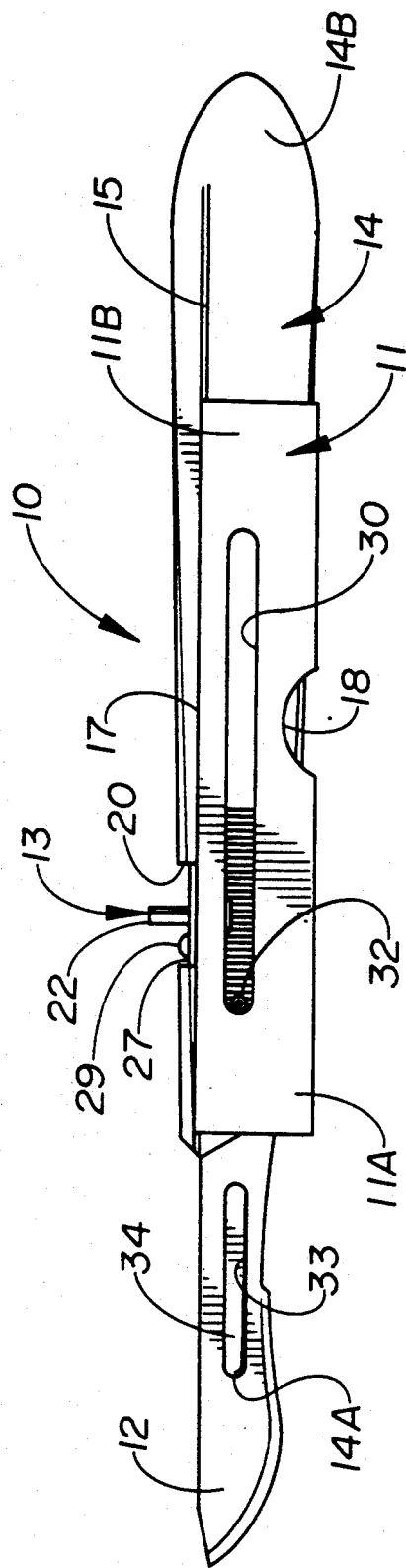
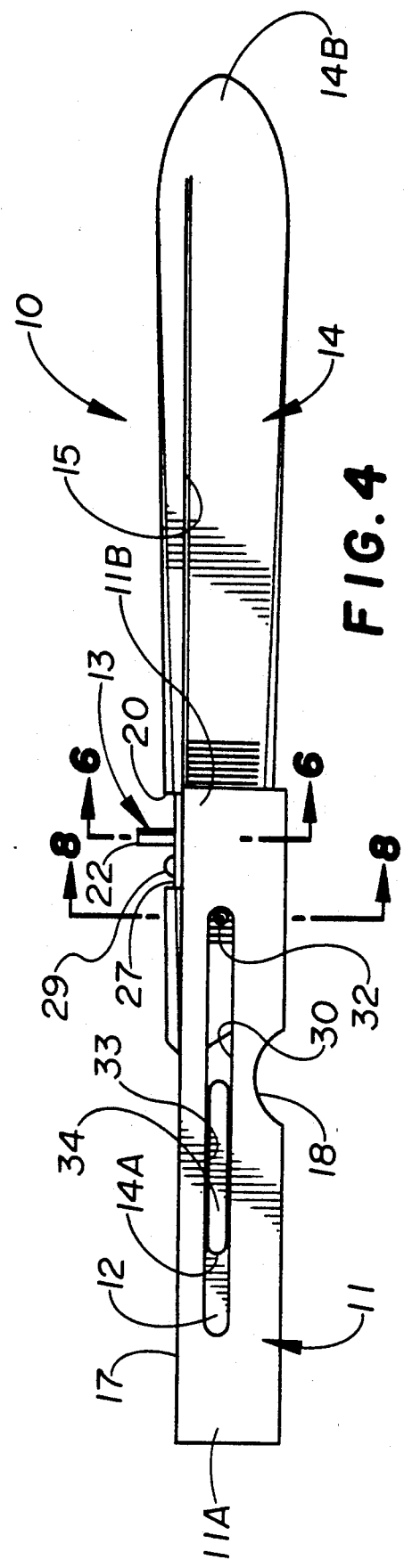

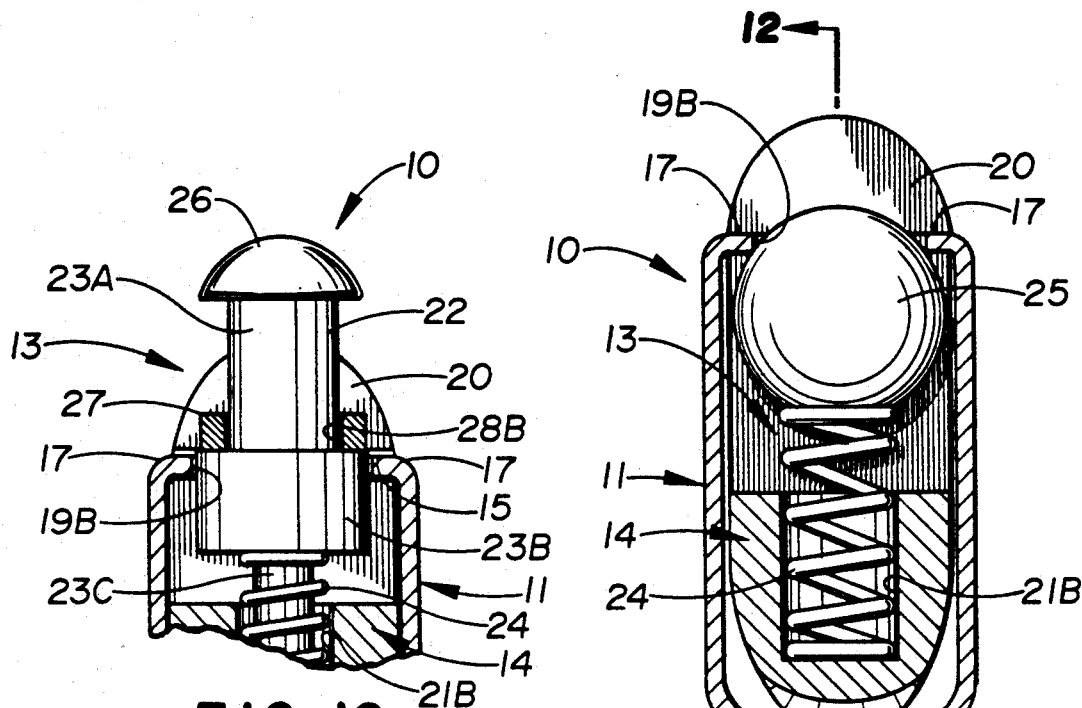
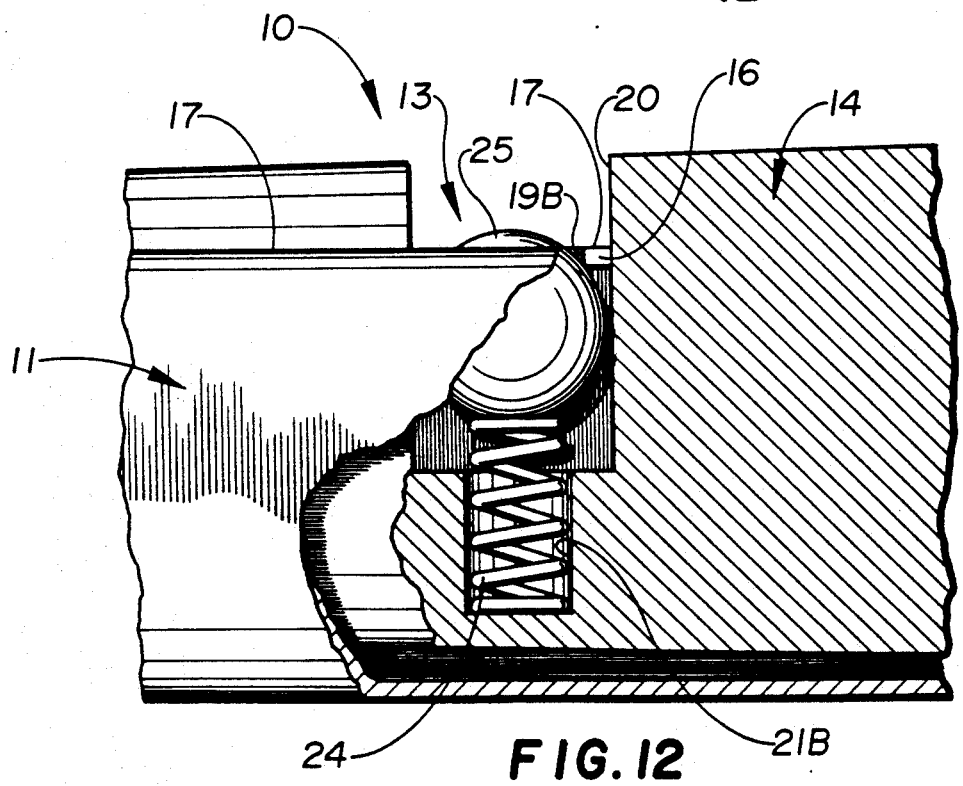

SURGICAL SCALPEL WITH RETRACTABLE GUARD

FIELD OF THE INVENTION

The present invention relates to surgical scalpels and, in particular, to surgical scalpels having retractable blade guards to protect against inadvertent nicks or cuts during a surgical procedure in an operating room.

BACKGROUND OF THE INVENTION

Surgical scalpels are regularly used by surgeons and other health care professionals for making incisions, as well as for other purposes, when a sharp instrument is required.

During routine surgical procedures, the operating room assistant (which may be a nurse or another doctor) has to "slap" the scalpel into the surgeon's hand. This must be done so that the surgeon can "feel" the scalpel's orientation, thereby permitting the surgeon to automatically grip the handle of the scalpel without taking his or her eyes away from the patient or operatory field. Because the surgeon does not remove his or her eyes from the operatory field, the surgeon is unable to see if the scalpel is being handed to him or her with the handle or blade of the scalpel in the palm of his or her hand. This can cause the surgeon's hand to be cut, thereby causing blood or body fluid exposure from the doctor to the patient and vice-versa. Moreover, when handing the scalpel back to the assistant, the surgeon is often unable to properly orient the scalpel. Thus, the assistant is often required to take the scalpel from the surgeon by gripping either the blade of the scalpel or a part of the scalpel that is in close proximity to the blade.

In both of the above cases, it is not uncommon for the surgeon's assistant, and sometimes even the surgeon, to be cut by the blade of the scalpel. Such cuts, in addition to being rather uncomfortable, can lead to the spreading of infection and disease. Concern over this situation has become especially acute since the appearance of the human immune deficiency virus (or "HIV"). Indeed, such cuts have already been blamed, by some health care providers, for cases of HIV infection in their profession. Consequently, some individual surgeons or health care providers have gone so far as to stop performing surgical operations altogether, rather than risk the chances of inadvertently contracting the deadly HIV from an infected patient.

Similar concerns are related to the Hepatitis B virus (or "HBV").

The risks associated with scalpel cuts during an operating room procedure are greater than those associated with needle sticks; but even there, the problem is becoming alarming. In a study made by the Needle Stick Surveillance Group of the C.D.C. (Communicable Disease Center) out of 3,978 known punctures from patients known to be HIV positive, 13 health care workers got infected or roughly 1 out of 300. Thus, from a single needle stick while treating an AIDS patient in an operating room or other environment, the chances are roughly 1 out of 300 that the surgeon, nurse or other individual health care provider will sero-convert and become HIV positive.

If a surgeon, nurse or assistant is cut by a scalpel while conducting a surgical procedure in an operating room (rather than a needle stick) the risk is much greater simply because, first, there is more blood involved and, secondly, the surface area of the wound produced is larger. In operating on an HIV positive patient, and even if the chances of becoming HIV positive from a scalpel cut are substantially the same as the needle sticks—roughly 1 out of 300–if the surgeon or nurse performs just one operating room procedure on an HIV-positive patient per day for 6 days a week, 50 weeks per year, then the chances of becoming HIV positive through an inadvertent cut in an operating room procedure are virtually guaranteed!

This situation has become so pronounced that some leading surgeons, as well as nurses and other individual health care providers, have abandoned their respective practices.

While protective gloves aid in reducing the chances of being cut during a surgical procedure, these gloves are by no means foolproof, and such cuts are still quite common. Even when two sets of gloves are utilized, full protection is not afforded to the health care provider, for many times the blade cuts right through both sets of gloves. Also, utilizing two sets of gloves at the same time reduces finger dexterity, thereby presenting problems during the intended surgical procedure and tending to reduce the effectivity thereof.

There have been numerous disclosures for providing protective blade guards for surgical scalpels which prevent inadvertent contact with the surgical blade prior to introduction of the scalpel into the sterile field where it will be used. Once the scalpel is in the sterile field, however, the protective blade guard is removed until the surgical procedure is finished. Examples of such disclosures (of which we are aware) are as follows:

| Inventor(s) | Patent No. |
| --- | --- |
| Leopoldi | 3,706,106 |
| Porat, et al. | 4,719,915 |
| Williams | 4,735,202 |
| Chase, et al. | 4,825,545 |
| Lipton | 4,985,034 |
| Baskas | 5,035,703. |

While these arrangements are useful for their intended purposes, none are readily adaptable for use during a surgical procedure in an operating room. In each of these devices, the protective blade guard is often a separate piece from the remainder of the scalpel. Thus, when using of the scalpel during the surgical procedure, the protective blade guard must be removed entirely therefrom. Such an arrangement requires a two-handed operation for the removal (and possibly the replacement) of the protective blade guard. One hand is necessary to grip the scalpel while the other hand is used to grip the guard. As such, these protective surgical blade guards are not practical for use during a standard surgical procedure in an operating room or equivalent area.

Preferably, a blade guard for a surgical scalpel should meet the following criteria:

(1) the protective guard should be retracted to expose the blade and, thereafter, advanced to cover the blade with the use of only one hand:

(2) the protective blade guard should be actively and solidly fixed (positively locked) in the position selected, so that the protective blade guard will not be accidentally dislodged or moved as a result of the necessary pressure that is exerted on the scalpel by the surgeon during the operating procedure;

(3) the doctor (or other user of the scalpel) must be able to readily and tactually identify the mechanism or element which permits (or releases) the protective blade guard to be moved, so that the protective blade guard can be placed in the selected position desired without the user thereof having to remove his or her eyes from the patient in order to visually observe the scalpel;

(4) the shape of the protective blade guard of the scalpel should substantially approximate the shape of the body of the scalpel by which the guard is carried, so that during use of the scalpel, the user may utilize a grip that substantially approximates the grip that is normally utilized, thereby providing the user with a good and comfortable "feel" when performing the surgical operating procedure; and (5) the scalpel should provide an auditory sensory means, whereby the user may be made aware that the protective blade guard has actually been locked into a desired selected position without the necessity of having to remove his or her eyes from the patient in order to visually observe the scalpel.

In U.S. Pat. Nos. 4,516,575 issued to Gerhard, et al., and 4,499,898 issued to Knepshield, et al., microsurgical scalpels designed for use in opthalmic surgery are disclosed wherein the surgical blade itself is movable in and out of the body of the scalpel. This is intended to control the depth of the incision in opthalmic surgery. While helping to give the surgeon a comfortable grip, neither of these devices meets the other requirements noted above for providing a guarded scalpel that is readily usable in standard operating procedures. In each of these scalpels, extension and retraction of the surgical blade is a two-handed operation, one hand being needed to hold the stationary part of the scalpel, and the second hand being needed to rotate the mechanism that moves the surgical cutting blade into a selected position desired. As noted above, such a two-handed operation makes these devices unadaptable for use in standard surgical procedures. Further, during use, pressure is placed on the surgical blade, which can result in accidental dislodgement or movement of the blade during the surgical procedure, a quite undesirable occurrence. Finally, it is noted that there is no auditory or tactile means whatsoever provided which would either identify the mechanism which permits the user to selectively position the surgical cutting blade or which would signal or indicate to a user that the blade is in the position desired without having to remove his or her eyes from the patient in order to visually observe the scalpel.

In U.S. Pat. No. 4,414,974 issued to Dotson. et al. a microsurgical knife is disclosed having a slidable shroud that can be moved into a forward position to protect the blade and rearwardly to allow use of the knife. However, this device is problematic in that no structures are provided thereon which fixedly and solidly retain and positively lock the shroud in place. Rather, the shroud is held in place only by reliance on a wedged fit. Since the shroud covers the body of the scalpel, during use of the scalpel in a standard surgical procedure, the shroud itself would be gripped by the user and pressure exerted directly thereon. Thus, the shroud of that device is readily susceptible to becoming accidentally dislodged or moved as a result of ordinary pressure being exerted thereon by the user during a surgical procedure. Furthermore, Dotson et al, requires a definite effort to move the shroud forwardly. As such, like the disclosures discussed above, this arrangement can require the user thereof to utilize two hands for moving the shroud, a situation which is not always possible nor desirable in an operating room ("O.R.").

In the O.R., time is of the essence and seconds count; the mental concentration and physical effort are intense; and distractions must be avoided at all times.

Finally, in U.S. Pat. No. 4,576,164 issued to Richeson, a microsurgical knife is disclosed which attempts to remedy the problems associated with Dotson et al by providing an arrangement for locking the sheath. While achieving this, locking the shroud of Richeson i place nonetheless involves a two-handed operation. One hand must hold the shroud, and the other must grip the body of the scalpel in order to effect the twisting motion necessary to lock the shroud. Hence, like many of the other disclosures, the scalpel of Richeson is not readily adaptable for use in operating room procedures. Further, there are no auditory or sensory means whatsoever provided in that arrangement which would permit the user thereof to be made aware that the protective blade guard has actually been locked into the selected position without having to remove his or her eyes from the patient in order to visually observe the scalpel.

Thus, it can be seen that there remains a need for a surgical scalpel that has a protective blade guard which is readily adaptable for use during a variety of surgical procedures in a standard operating room, and which meets the objectives and desired criteria noted above.

SUMMARY OF THE INVENTION

It is a primary object of the present invention to provide a surgical scalpel which has a protective guard that is readily adaptable for use during a variety of surgical procedures in a standard operating room or similar environment.

It is another object of the present invention to provide such a surgical scalpel having a movable protective guard that is readily retracted to expose the blade, and thereafter repositioned over the blade, with the use of only one hand.

It is still another object of the present invention to provide such a surgical scalpel having a movable blade guard which is actively and solidly fixed and positively locked in the position selected, so that the guard will not be accidentally dislodged or moved as a result of the necessary pressure that is normally exerted thereon by the user while gripping the scalpel.

It is a still further object of the present invention to provide such a scalpel having a movable guard which permits the surgeon (or other user of the scalpel) to be able to readily and tactually identify the mechanism or element which permits the guard to be moved, so that the guard can be placed in the selected position desired without the necessity of the user having to remove his or her eyes from the patient in order to visually observe the scalpel.

It is yet still further object of the present invention to provide such a scalpel having a movable guard wherein the shape of the guard substantially approximates the shape of the body of the scalpel by which it is carried, so that during use of the scalpel, the user may utilize a grip that substantially approximates the grip that is normally utilized, thereby providing the user with a good and comfortable "feel" when performing the surgical procedure.

It is a further object of the present invention to provide a scalpel that includes an auditory sensory means, whereby the user may be made aware that the guard has actually been locked into the selected position without the necessity of having to remove his or her eyes from the patient in order to visually observe the scalpel.

It is a still further object of the present invention to provide such a surgical scalpel, wherein the blade thereof may be easily and conveniently removed and replaced.

In accordance with the teachings of the present invention, an improved surgical scalpel is disclosed. This improved scalpel includes a body having a forward end and a rearward end. A surgical cutting blade is removably secured to the forward end of the scalpel body and projects forwardly thereof. A blade guard is carried by the body of the scalpel for selective longitudinal sliding movement thereon between a forward, extended position and a rearward, retracted position. In its forward, extended position, the guard extends over the blade, thereby selectively covering the blade and protecting the user or handler from inadvertent cuts. In its rearward, retracted position, the guard exposes the blade and permits normal use of the scalpel. The guard may be slidably moved longitudinally of the body of the scalpel—with the use of only one hand—and means are provided for removably locking the guard in its respective positions. In this manner, the guard will not be accidently dislodged during the normal gripping pressure exerted on the scalpel.

In a preferred embodiment, the scalpel further includes a release means for selectively unlocking the guard. This release means extends outwardly of the guard and is readily and tactually identified and utilized without the necessity for the user to visually observe the scalpel. Moreover, the release means is operable with one hand, so that the guard may be unlocked, released and longitudinally slidably moved between its forward and rearward positions, respectively, with the use of only one hand.

Preferably, the guard is formed so as to substantially approximate the shape of the body of the scalpel. In this manner, the surgeon may utilize a grip that substantially approximates the grip that is normally utilized so as to provide the surgeon with a comfortable "feel" during use of the scalpel.

Moreover, the scalpel preferably includes an auditory sensory warning means (such as a "click") indicating that the guard has been locked into its desired selected position. In this manner, the surgeon or other user may be made aware that the protective guard has actually been locked into its desired selected position without the necessity for visually observing the scalpel. In a preferred embodiment, a resiliently-biased detent means is formed between the body of the scalpel and the guard for removably securing the guard in its respective forward and rearward positions.

Viewed in another aspect, the present invention provides a guard for the blade of a surgical scalpel of the type having a main body portion including a forward section upon which the blade is removably mounted. The guard comprises a substantially U-shaped channel including a pair of parallel side walls connected by a bottom wall, such that the guard closely straddles the main body portion of the scalpel and does not interfere with the normal use of the scalpel during a procedure performed in an operating room. Means are provided for slidably mounting the guard on the body of the scalpel for limited movement longitudinally of the body of the scalpel, thereby defining a first extended position covering the blade and a second retracted position exposing the blade. With this structure, the surgeon, nurse or assistant in the operating room may move the guard from one position to another in a one-handed movement without taking his or her eyes away from the patient. Moreover, the blade guard provides a tactile indication of the respective position of the guard on the body of the scalpel, so that either the surgeon or the nurse in the operating room does not have to take his or her eyes away from the patient while passing the scalpel from one to another during the operating procedure, but rather will know instinctively from the feel of the scalpel itself, thereby preventing the usual cuts or nicks normally encountered in passing a surgical scalpel from the assistant to the surgeon and vice versa during an operating procedure. Accordingly, the present invention substantially reduces the risk of the surgeon, nurse or assistant inadvertently acquiring an infectious disease, such as HIV or HBV, in the operating room or similar medical environment.

These and other objects of the present invention will become readily apparent from a reading of the following description of the present invention, taken in conjunction with the enclosed drawings.

BRIEF DESCRIPTION OF THE DRAWINGS

FIG. 4 is a side elevation of the scalpel of the present invention with the protective guard in a first extended (advanced) position to cover the blade, thereby protecting both the surgeon and the assistant (or nurse) during a surgical procedure.

FIG. 5 is a side elevation of the scalpel of the present invention with the protective guard in a second, retracted position, thereby exposing the blade for use during a surgical procedure.

FIG. 10 corresponds substantially to FIG. 6, but shows a cap or button on the releasable detent means for the blade, thereby providing a preferred tactile means, so that the guard can be slid longitudinally of the scalpel body.

FIG. 11 is an alternate embodiment of the releasable detent means for the guard.

FIG. 12 is a cross-sectional view thereof, taken along lines 12—12 of FIG. 11.

in FIGS. 13A-13D, the thumb engages the releasable detent pin (or button) and the forefinger is received in the cut-out formed in the bottom wall of the U-shaped sliding guard to alternately retract and advance the guard.

GENERAL DESCRIPTION OF THE PREFERRED EMBODIMENTS

Figure 1:
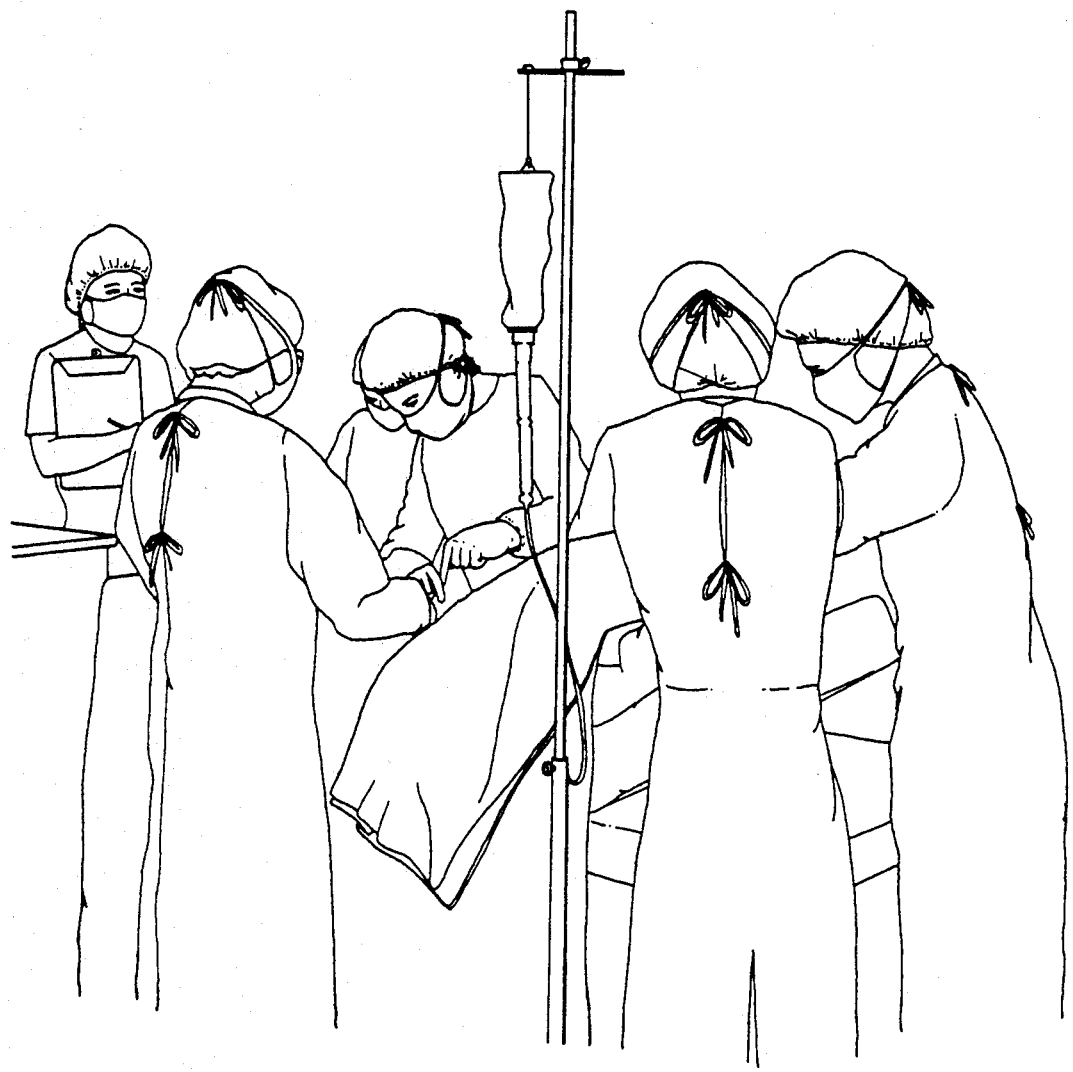
FIG. 1 is a perspective view of an operating room or theater where the improved surgical scalpel, equipped with the protective blade guard of the present invention, will be utilized.

While reference to FIG. 1, the improved scalpel of the present invention finds particular utility in an operating room ("O.R.") or other similar medical environment.

Figure 2A:
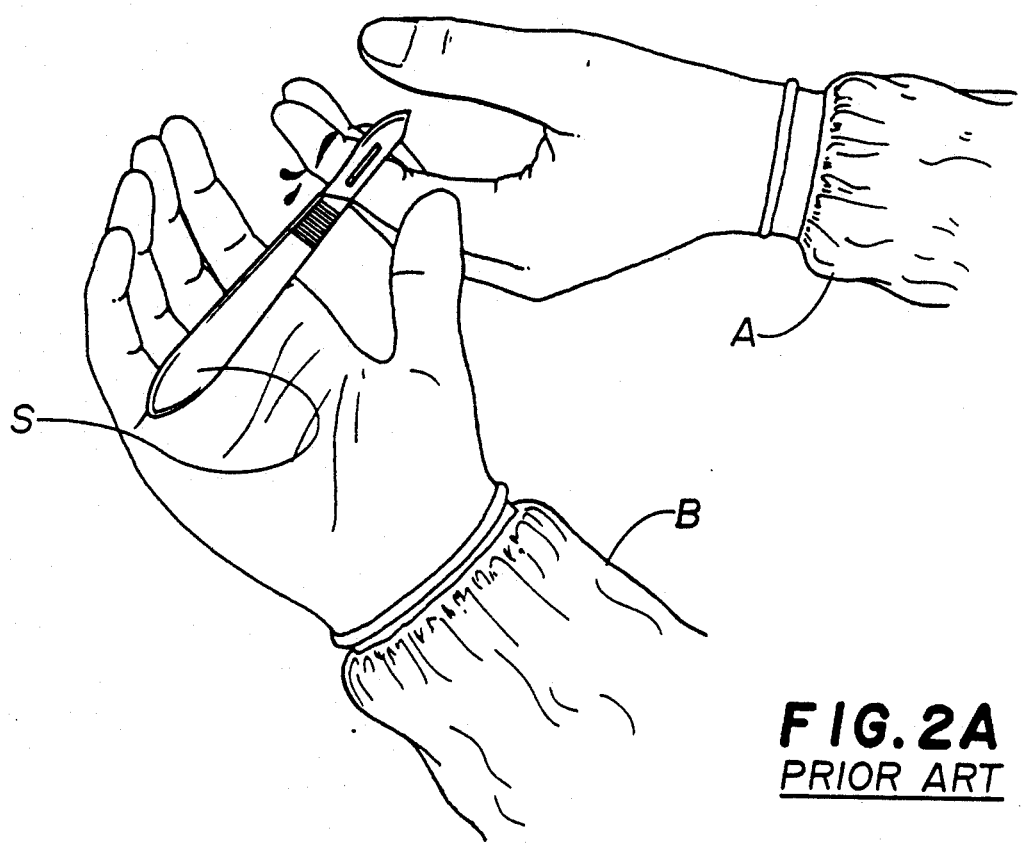
FIG. 2A is an enlarged view of a conventional scalpel, illustrating how an assistant may be cut or nicked when the surgeon passes the scalpel to the assistant while performing an operating procedure.
Figure 2B:
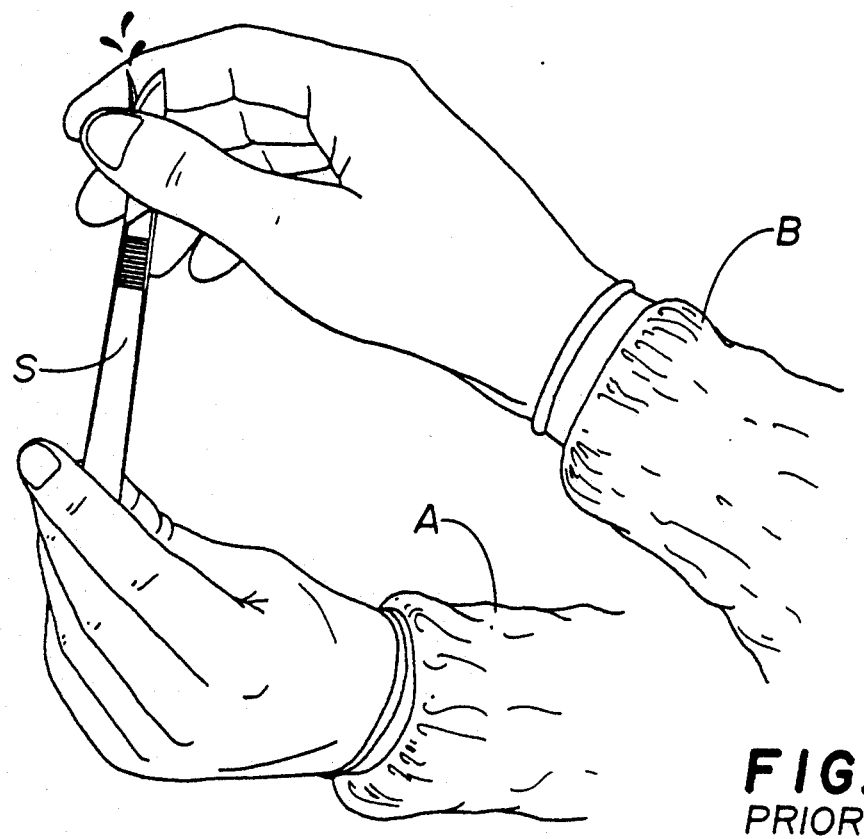
FIG. 2B is an enlarged view of a conventional scalpel, corresponding substantially to FIG. 2A, but showing how the surgeon may be cut or nicked when the assistant passes the scalpel to the surgeon.

The problems inherent in the prior art, as previously discussed, are illustrated in FIGS. 2A and 2B, respectively. There, a conventional (non-guarded) scalpel S is being passed from the nurse (or assistant) a to the surgeon, B as in FIG. 2A, and from the surgeon B to the nurse (or assistant) a as in FIG. 2B. As previously noted, the surgeon and the assistants are often cut while transferring the conventional non-guarded scalpel S with its blade exposed, and the risks and consequences of being so cut are indeed grave and are escalating rapidly.

Figure 3A:
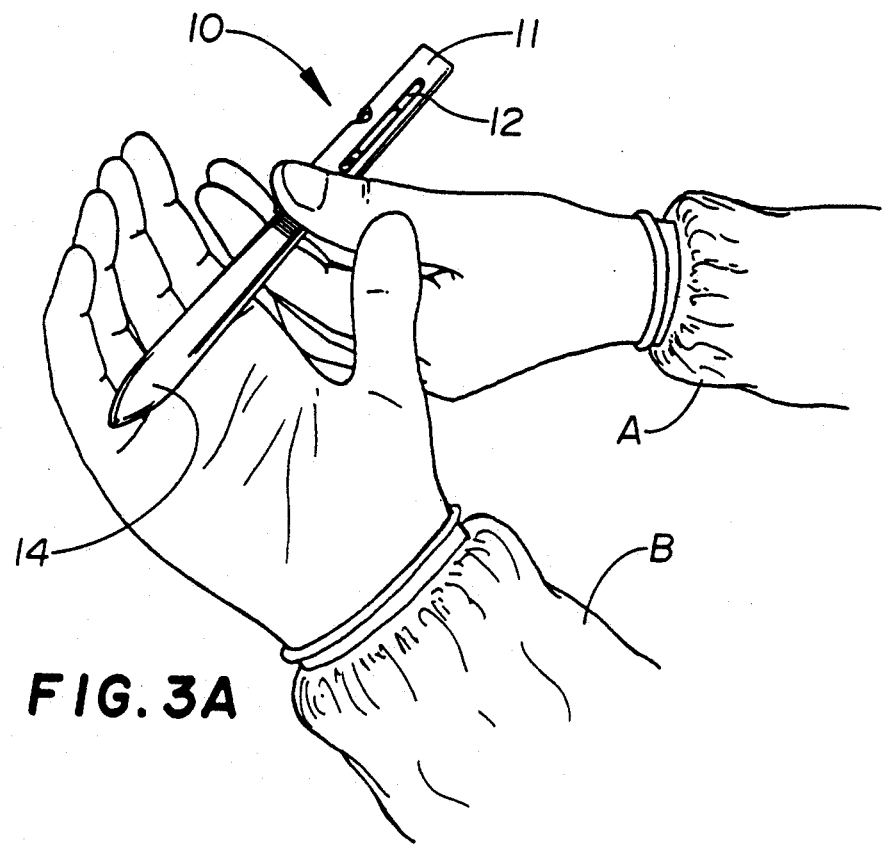
FIG. 3A illustrates how the improved scalpel of the present invention protects the assistant's hands when passing the scalpel to the surgeon during an operation.
Figure 3B:
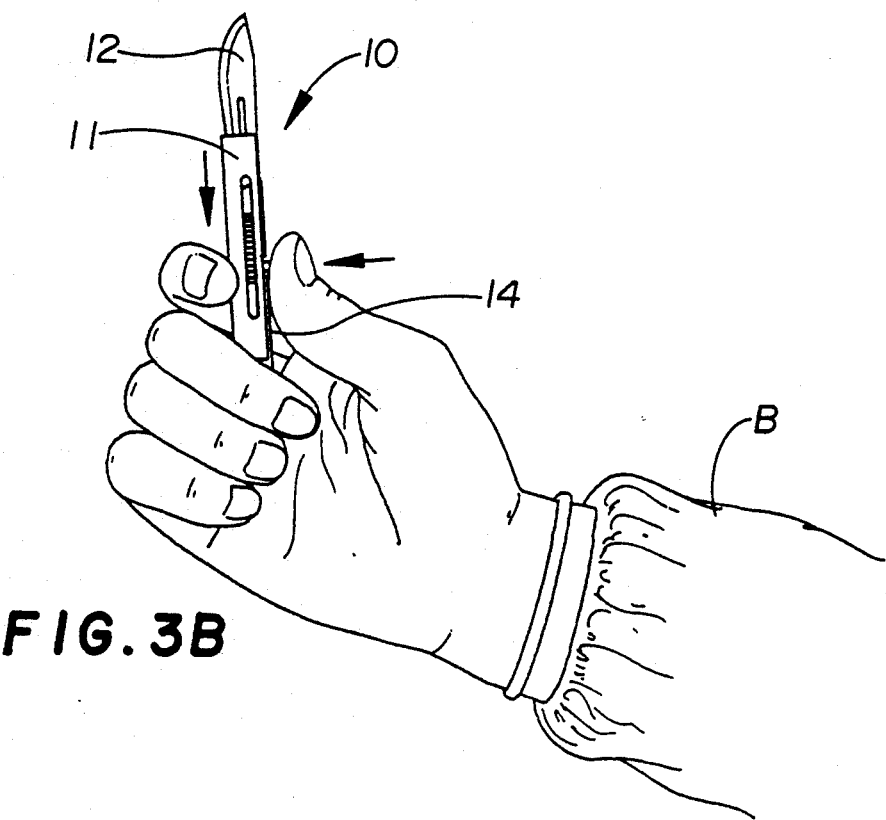
FIG. 3B illustrates how the improved scalpel of the present invention is easily and conveniently retracted—with one hand—by the surgeon, so that the blade of the scalpel is exposed for permitting immediate use thereof.

With reference to FIGS. 3A and 3B, these problems are remedied by the improved scalpel 10 of the present invention equipped with a protective retractable guard 11 for the blade 12. This guard 11 is carried by the body of the scalpel 10 for selective longitudinal movement of the guard 11 on the body of the scalpel 10 between a forward, extended position and a rearward retracted position—especially with the use of only one hand—and without the surgeon or assistant having to remove his or her eyes from the patient.

With reference to FIGS. 4-9, a resiliently-biased detent means 13 is formed between the improved scalpel 10 and the guard 11. This detent means 13 releasably locks the guard 11 in its selected extended and retracted positions, respectively. Preferably, the release means for the detent mechanism may be tactually located (or identified) and utilized easily and conveniently and with a "click" or other auditory means that signals the user when the blade guard 11 has been locked into its selected position.

In its forward, extended position, the retractable guard 11 of the present invention extends over and substantially surrounds and covers the blade 12 (as shown more clearly in FIG. 4). In this position, the scalpel 10 may be safely passed from the surgeon to the assistant (and vice versa) without accidentally cutting or nicking either the surgeon or assistant (as shown more clearly in FIG. 3A)

Advantageously, the resiliently-biased detent means 13 may be used to easily and selectively slidably move the guard 11 rearwardly of the blade 12 and into its retracted position, as shown more clearly in FIG. 5, such that the blade 12 is substantially exposed (or uncovered) for use during the surgical procedure in the operating room. The resiliently-biased detent means 13 permits each user or handler of the scalpel 10 to retract the guard 11—with the use of only one hand and without the necessity of having to remove his or her eyes from the patient in order to visually observe the scalpel 10—as shown more clearly in FIG. 3B.

Figure 3C:
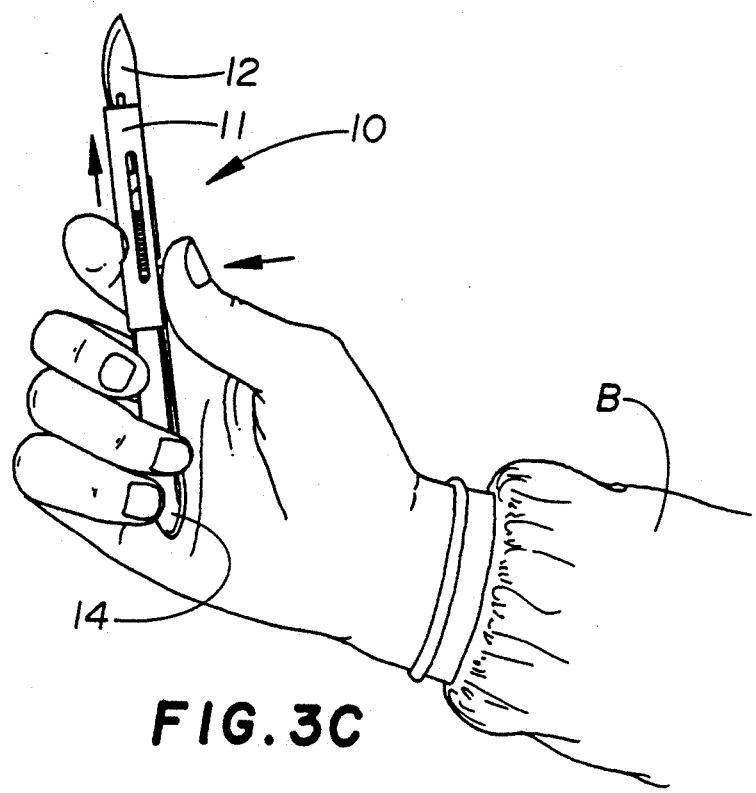
FIG. 3C illustrates how the protective guard of the improved scalpel of the present invention is easily and conveniently advanced—again, with one hand—by the surgeon, so that the blade of the scalpel is covered.

Once the surgeon has finished using the scalpel 10, the guard 11 may then, by releasing the resiliently-biased detent means 13, be easily and selectively slidably moved back into its extended position, so as to cover the blade 12 and prevent inadvertent and accidental engagement with the blade 12. It is noted that the resiliently-biased detent means 14 permits the users (such as a surgeon) to extend the guard 11 into its position of covering the guard 11 with the use of only one hand and without the necessity of having to remove his or her eyes from the patient in order to visually observe the scalpel 10 (as shown more clearly in FIG. 3C).

Figure 3D:
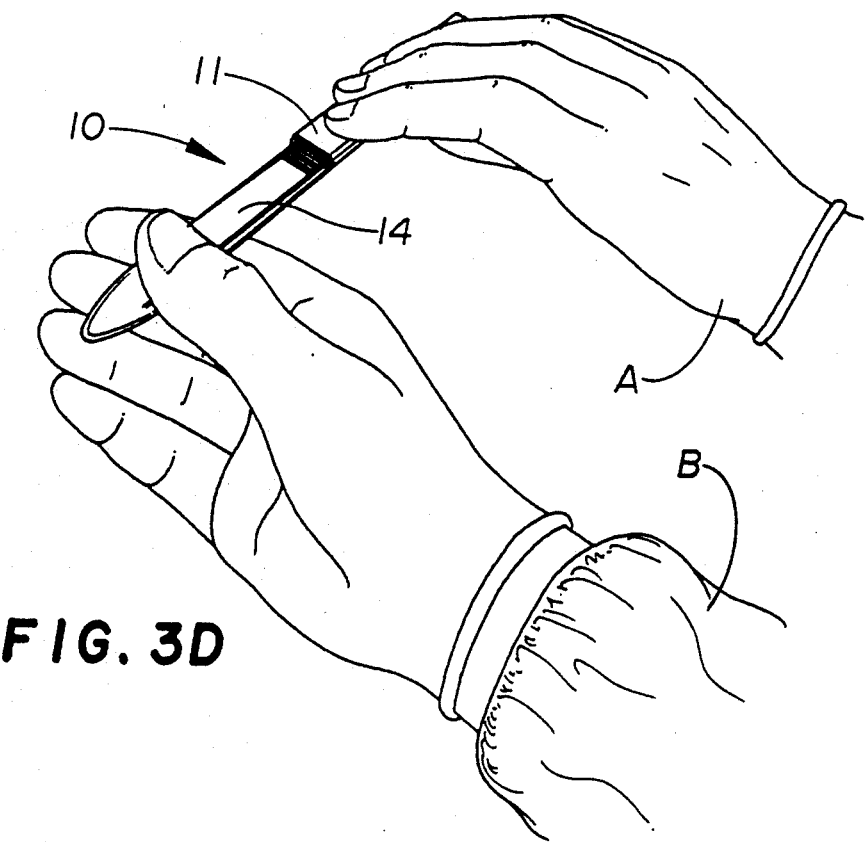
FIG. 3D illustrates how the scalpel of the present invention protects the assistant's hands when the scalpel is passed by the surgeon to the assistant.

With the retractable guard 11 selectively replaced in its forward, extended position the blade 12, the scalpel 10 may once again be safely passed from the user (such as the surgeon) to the assistant without cutting either the assistant or the surgeon (as shown more clearly in FIG. 3D).

Figure 9:
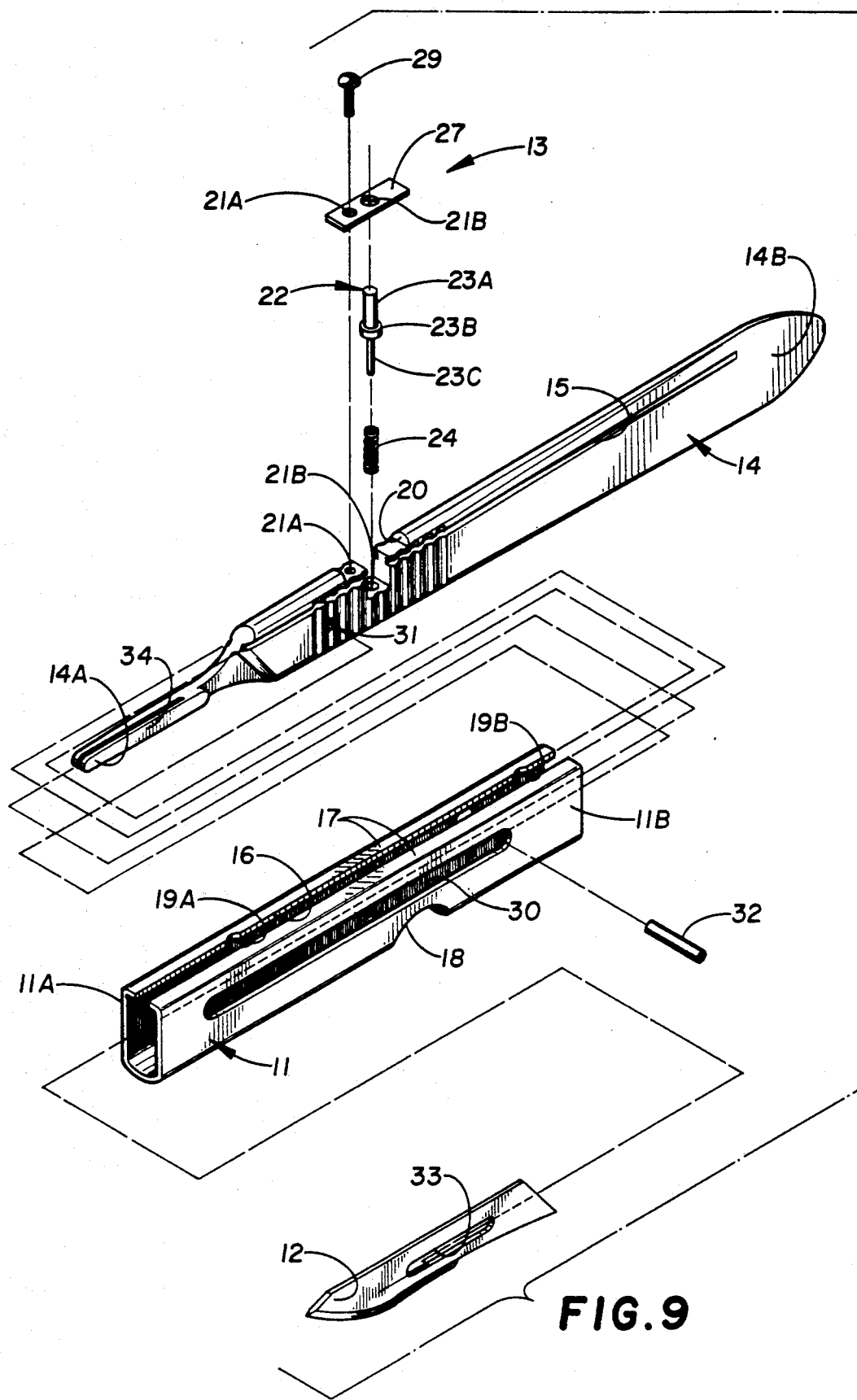
FIG. 9 is an exploded perspective view of the improved surgical scalpel of the present invention and its protective blade guard.
Figure 13A:
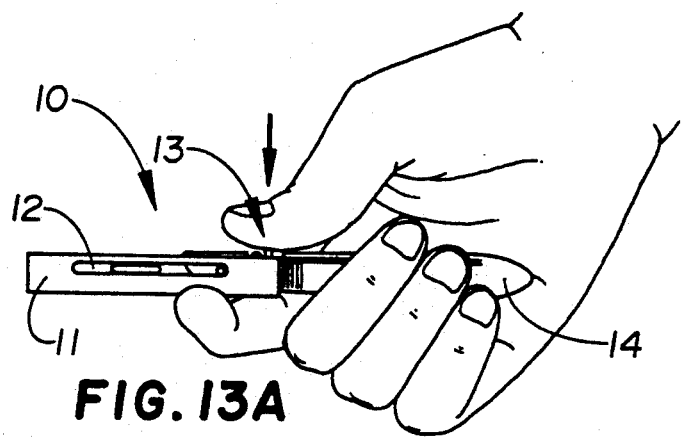
FIGS. 13A-13D show, respectively, the manner in which the sliding blade guard may be manually retracted to expose the blade on the scalpel, and then advanced to cover the blade to protect against inadvertent cuts and nicks normally occasioned in transferring the scalpel from the nurse to the surgeon, and vice versa, during a surgical procedure.
Figure 13B:
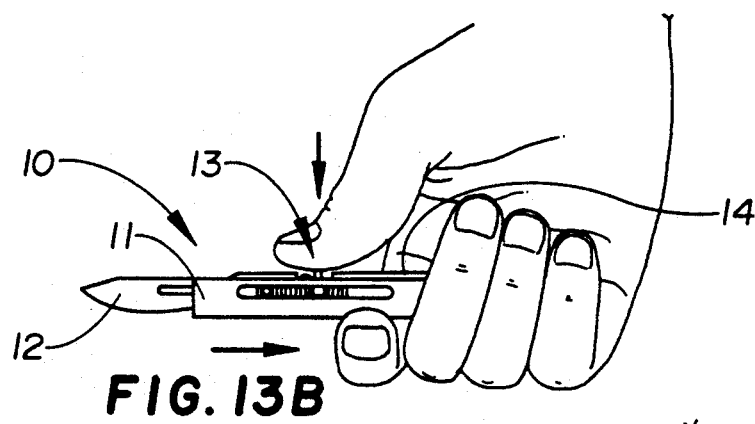
Figure 13C:
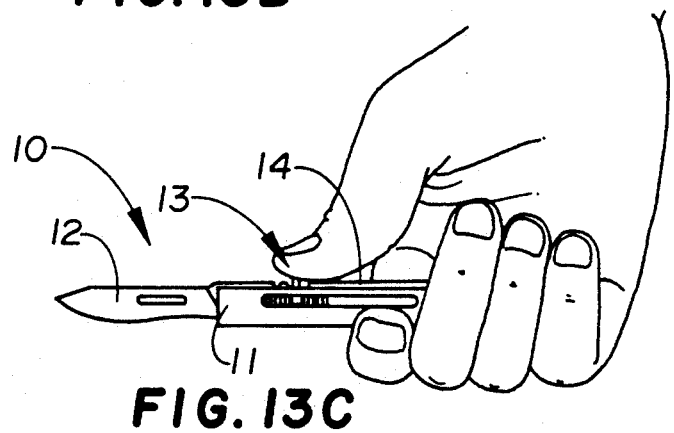
Figure 13D:
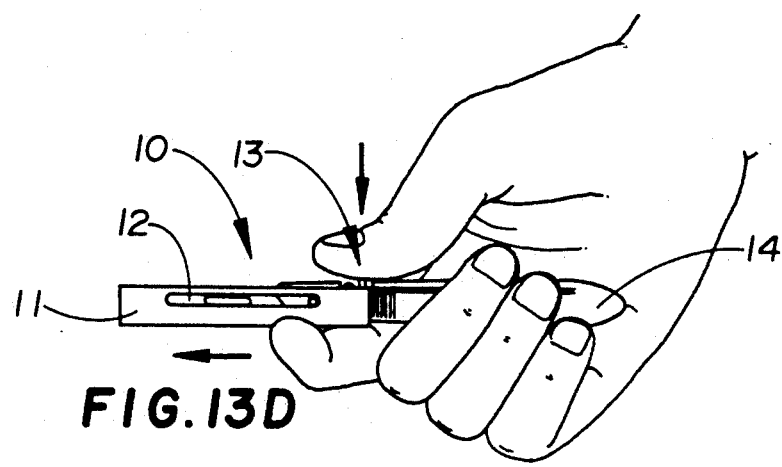
Figure 14A:
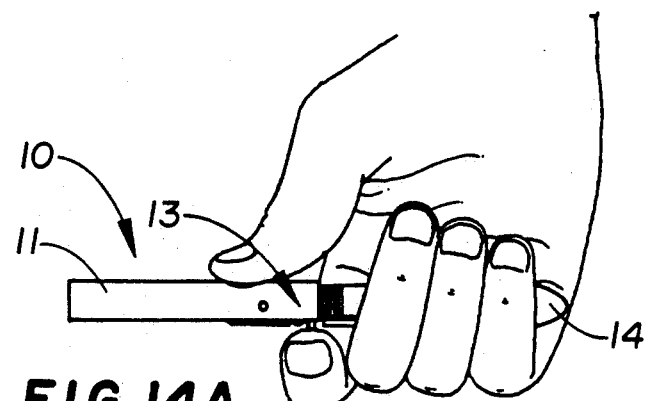
FIGS. 14A-14D correspond substantially to that of FIGS. 13A-13D, but show an alternate manner for selectively and alternately retracting and advancing the sliding guard, wherein the forefinger releases the detent pin, and wherein the thumb engages the cut-out in the bottom wall of the guard; the surgeon may then use the scalpel to cut in a generally upwardly direction or may pivot his or her wrist to cut in a generally downwardly direction, as desired.
Figure 14B:
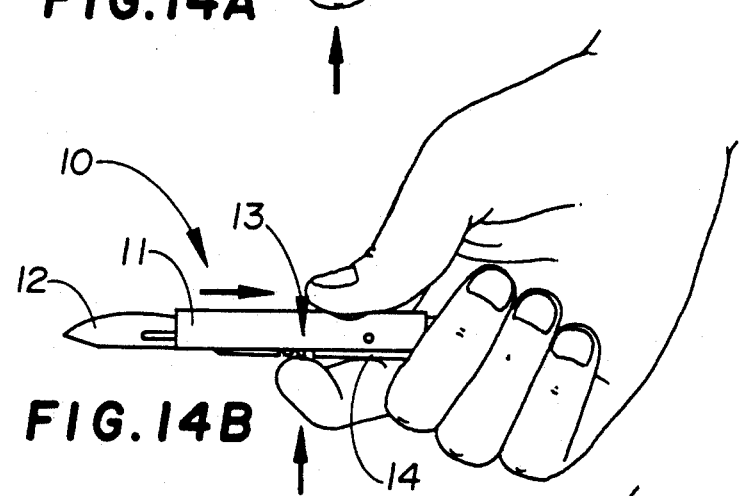
Figure 14C:
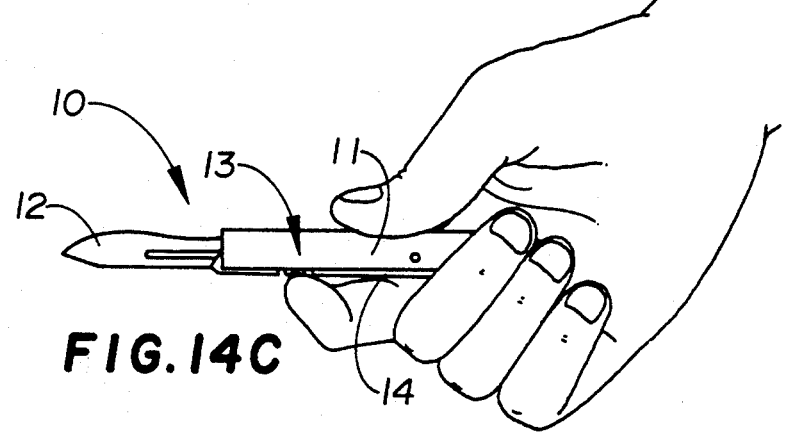
Figure 14D:
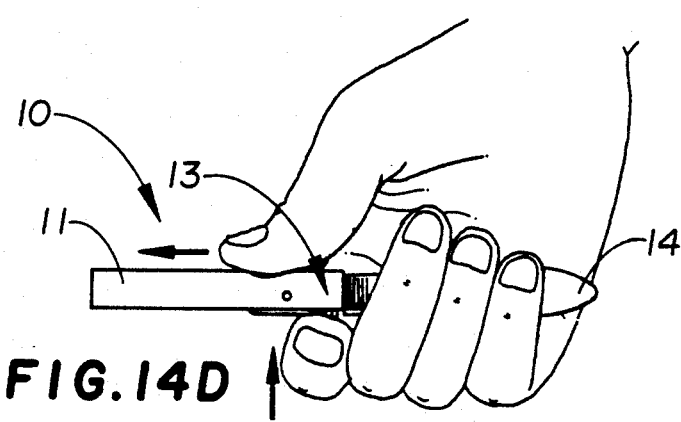

With particular reference to FIGS. 4, 5 and 9, the improved scalpel 10 of the present invention (with its protective blade guard 11) has an elongated body 14 having a forward portion terminating in a forward end 14A and a rearward portion terminating in a rearward end 14B. Preferably, the body 14 of the scalpel 10 of the present invention is substantially rectangular in shape, being substantially symmetrical about a longitudinal axis, so that the shape of the body 14 substantially approximates or mirrors the shape of conventional scalpels. Such a shape facilitates a ready and convenient use of the scalpel 10, providing the user thereof with a "feel" that is substantially the same as the "feel" provided by conventional scalpels. In this manner, when using the scalpel 10 of the present invention, the user may grip the scalpel 10 in the same manner as he or she would normally grip a conventional scalpel.

The blade guard 11 of the present invention is also elongated in shape, having a forward portion terminating in a forward end 11A and a rearward portion terminating in a rearward end 11B. Like the body 14 of the scalpel 10, the blade guard 11 is preferably substantially rectangular in shape, being substantially symmetrical about a longitudinal axis, so that the shape of the guard 11 substantially approximates or mirrors the shape of the body 14 of the scalpel 10 (and hence the shape of conventional scalpels, as noted herein).

Preferably, the blade guard 11 is in the form of an open-ended inverted U-shaped channel (see FIG. 9) and is slidably disposed over at least a portion of the body 14, such that the guard 11 is carried on the body 14 of the scalpel 10, and such that the longitudinal axis of the guard 11 is substantially aligned with the longitudinal axis of the scalpel 10.

The shape of the guard 11 facilitates the use of the scalpel 10 and does not interfere with the "feel" that is provided by the scalpel 10 (as previously noted). In this manner, when using the scalpel 10 of the present invention, the user may grip the scalpel 10, including the guard 11 disposed thereon, in the same manner as he or she would normally utilize to grip a conventional scalpel, so as to provide the user with a comfortable "feel" during use thereof.

The guard 11 of the present invention is carried by the body 14 for selective longitudinal sliding movement of the guard 11 on the body 14 between the forward (extended) position (FIG. 4) and the rearward (retracted) position (FIG. 5) with the use of only one hand, and this is a significant improvement of the present invention over the available prior art.

With reference again to FIGS. 4-9, to provide the selective longitudinal sliding movement of the guard 11 on the body 14 of the scalpel 11, the body 14 of the scalpel 10 has a pair of longitudinal guide tracks 15 formed therein. These guide tracks 15 are formed between the forward end 14A and the rearward end 14B of the body 14 of the scalpel 11. A respective one of said tracks 15 is formed on either side of the body 14.

The top portion of the blade guard 11 (which is in the form of an inverted U-shaped channel) has a longitudinal slot 16 formed therein; and the slot 16 has respective edges defining respective in-turned guide flanges 17. Each of these flanges 17 is received in a respective guidetrack 15, thereby facilitating a one-hand selective sliding longitudinal movement of the guard 11 on the body 14 of the scalpel 10.

To further facilitate the one-handed sliding longitudinal movement of the guard 11 on the body 14 of the scalpel 10, the guard 11 includes a thumb cut-out portion 18 formed therein. Preferably this cut-out 18 is formed in the bottom wall of the guard 11, near where the user's thumb would normally be located during use of the scalpel 10. Positioned thusly, the user may easily insert his or her thumb into the cut-out 18 for slidably moving the guard 11 forwardly and rearwardly, as desired, during use of the scalpel. In this manner, the one-handed longitudinal sliding movement of the scalpel 10 by the user is further facilitated.

In order to achieve the above-mentioned goals of permitting the safe handling of the scalpel and the one-handed retraction and extension of the guard 11—without the necessity of visual observation—the scalpel 10 of the present invention includes a resiliently-biased detent means 13 that is formed between the body 14 of the scalpel 10 and the guard 11. This detent means 13 provides the following:

(1) a locking means formed between the scalpel 10 and the guard 11 which selectively locks the guard 11 in the respective retracted and extended positions thereof, so that the guard 11 will not be accidently dislodged or moved as a result of ordinary pressure being exerted thereon by the user while gripping the scalpel;

(2) a release means between the scalpel 10 and the guard 11 that may be tactually and readily identified and utilized (or operated) by a user with only one hand (and without the necessity of the user having to visually observe the scalpel 10) for selectively unlocking the blade guard 11, so that the guard 11 is released for the longitudinal sliding movement thereof between the retracted (rearward) and the extended (forward) positions thereof; and (3) an auditory warning means formed between the scalpel 10 and the guard 11 that provides an auditory signal (a click) when the guard 11 has been locked into the selected (extended or retracted) positions thereof, whereby the user may be made aware that the guard 11 has actually been locked into the selected (retracted or extended) positions without the necessity of the user having to visually observe the scalpel 10.

The resiliently-biased detent means 13 of the present invention includes a pair of transverse recesses or pockets 19A and 19B that are formed in the slot 16 of the blade guard 11. One of these pockets, 19A, is formed in the forward portion of the guard 11. The other of the pockets, 19B, is formed in the rearward portion of the guard 11. Pockets 19A and 19B provide a pair of locking detent means in the guard 11. As shall be discussed at length below, the pockets 19A and 19B receive therein a resiliently-biased locking means, so that the guard 11 is selectively locked, respectively, into its respective extended and retracted positions.

The resiliently-biased detent means 13 of the present invention is received at least partially within a stepped-shaped cut-out 20 formed in the body 14 of the scalpel 10. However, it should be clearly understood by those skilled in the art, that such a stepped shape is by no means necessary.

Formed in the body 11 of the scalpel 10, where the cut-out 20 is formed, are a pair of respective blind-ended bores 21A and 21B. One of these bores (bore 21A) is located forwardly of the other bore (bore 21B). However, once again, it should be expressly understood that this is not critical.

Received in the rearward bore 21B is a resiliently-biased locking means, such that the locking means is carried by the body 11 of the scalpel 10.

Figure 6A:
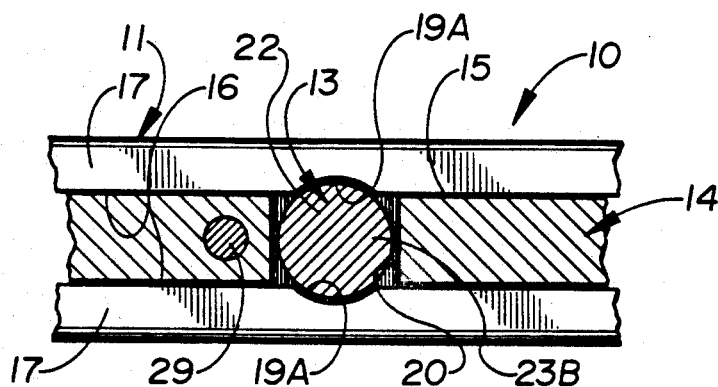
FIG. 6A is a cross-sectional view thereof, taken across the lines 6A—6A of FIG. 6, and showing the annular shoulder or collar on the spring-loaded detent pin being received in the respective detent pockets formed on the slidable blade guard.
Figure 6:
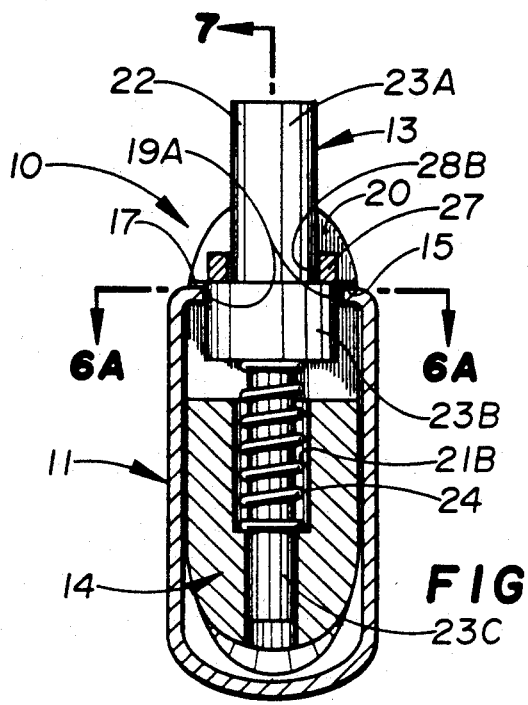
FIG. 6 is a cross-sectional view, taken along lines 6—6 of FIG. 4 and drawn to an enlarged scale, and showing the manually-releasable detent means for the guard.
Figure 7:
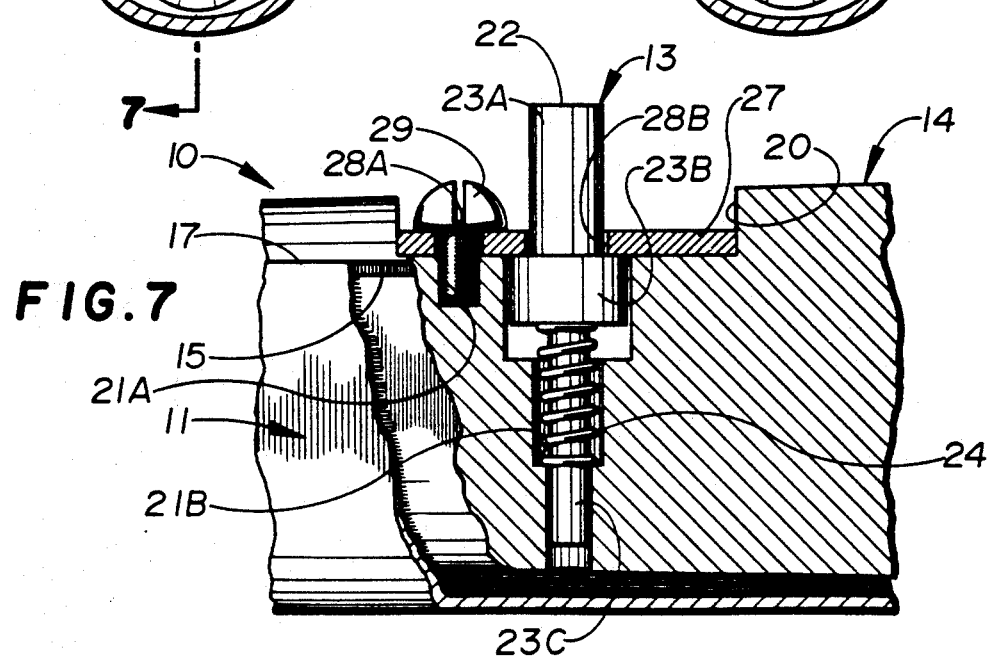
FIG. 7 is a cross-sectional view taken along lines 7—7 of FIG. 6 and drawn to an enlarged scale, and showing the means for retaining the detent means on the body of the scalpel.

With particular reference to FIGS. 6, 6A and 7, the resiliently-biased locking means 13 includes a locking member preferably in the form of a locking pin 22. The locking pin 22 includes an (upper) release extension 23A. As shall be discussed further below, this release extension 23A forms part of the release means of the present invention. Adjacent to the release extension 23A, the locking pin 22 further includes an annular shoulder 23B to be received in the locking detent pockets 19A and 19B formed in the slot 16 of the guard 11. Finally, the locking pin 22 also includes a lower stem 23C that is adjacent to the annular shoulder 23B and extends downwardly therefrom oppositely from the release extension 23A.

When assembled, a portion of the abutment shoulder 23B and the lower stem 23C are substantially disposed in the bore 21B with the release extension 23A extending outwardly from the body 14 of the scalpel 10.

Also disposed in the bore 21B, so as to be between the body 14 of the scalpel 10 and the annular shoulder 23B of the locking pin 22, is a biasing spring 24. In this manner, the biasing spring 24 abuts both the body 14 of the scalpel 10 and the annular shoulder 23B of the locking pin 22 for constantly resiliently-biasing the locking pin 22 outwardly. It is preferred that the biasing spring 24 be received around the lower stem 23C of the locking pin 22 with one end of the biasing spring 24 abutting the body 14 of the scalpel 10 and a second end abutting the bottom surface of the annular shoulder 23B of the locking pin 22. Thus, the locking pin 22 is constantly resiliently-biased outwardly thereof.

The resilient outward-biasing action of the spring 24 on the locking pin 22 constantly urges the annular shoulder 23B outwardly and into the respective locking detents 19A and 19B that have been aligned therewith by the selective sliding movement of the guard 11. When the annular shoulder 23B is so received or disposed in the detent pockets 19A and 19B, the guard 11 is releasably locked into, respectively, its extended and retracted positions. It is noted that the width of the slot 16 is substantially smaller than the width of the annular shoulder 23B.

Thus it will be appreciated that the bore 21A, locking pin 22 (and particularly the annular shoulder 23B and the lower stem 23C), the biasing spring 24 and the locking detent pockets 19A and 19B define the locking means of the present invention. This locking means provides for locking the guard 11 in its respective retracted and extended positions. In this fashion, the guard 11 will not be accidentally dislodged or moved as a result of ordinary pressure thereon by the user while gripping the scalpel 10 during the normal use thereof.

If desired, the locking means may, alternatively, be in the form of a ball-spring detent (FIGS. 11 and 12). In such a case, the locking pin 22 is replaced by a ball 25 that is supported by the second upper end of the biasing spring 24, so as to be continually upwardly resiliently-biased thereby.

The resilient outward-biasing action of the spring 24 on the locking pin 22 further constantly urges the release extension 23A outwardly beyond both the blade guard 11 and the body 14 of the scalpel 10. In this fashion, the release extension 23A defines a tactile means, whereby the user of the scalpel 10 may easily and conveniently locate the release means without the necessity of having to remove his or her eyes from the patient in order to visually observe the scalpel 10.

It is noted that the width of the slot 16 is greater than the width of the release extension 23A. In this manner, the release extension 23a is received through the slot, so that the guard 11 may be slidingly moved with the release extension 23A extending therethrough.

Positioned as described above, when the users of the scalpel 10 wish to release the blade guard 11 for the sliding movement thereof between the respective extended and retracted positions, they need only to tactually locate the outwardly-extending release mechanism 23A and then push downwardly on the release extension 23A of the locking pin 22, so as to overcome the biasing effect (force) of the spring 24 and downwardly clear the annular shoulder 23B from the respective detent pocket 19A or 19B in which it may be positioned. Once the shoulder 23B has been so dislodged, the guard 11 may be slidingly moved without further pressure being applied thereon. Thus a release means is defined which may be operated or actuated by a user utilizing only one hand.

Preferably, the release extension 23A of the locking pin 22 has an enlarged rounded end or head 26 formed thereon (FIG. 10). This rounded end (head) 26 facilitates the downward pushing of the locking pin 22 against the biasing action of the biasing spring 24 for disengaging the release extension 23A of the locking pin 22 from the locking detent pockets 19A and 19B, so that the guard 11 may be selectively moved between its respective first and the second positions.

Disposed over the cut-out 20 is a retaining plate 27. Plate 27 has a pair of apertures 28A and 28B formed therein. When disposed over the cut-out 20, the (forward) aperture 28A is substantially aligned with the forward bore 21A, and the (rearward) aperture 28B is substantially aligned with the rearward bore 21B.

The upward movement of the locking pin 22 under the action of the biasing spring 24 is restrained by the shoulder 23B of the pin 22 abutting against the bottom surface of the plate 27 with the release extension 23A extending outwardly therethrough, when the pin 22 is biased outwardly (as shown more clearly in FIG. 7). In this arrangement, the release extension 23A extends through the aperture 28B aligned therewith, so as to extend outwardly above the plate 27 and, as was noted above, provide a tactile means whereby the user of the scalpel 10 may locate and utilize the release means without the necessity of having to remove his or her eyes from the patient in order to visually observe the scalpel 10.

Received downwardly through the aperture 28A and the forward bore 21A aligned therewith, so as to be threadably engaged therein, is a threaded screw 29 (as shown more clearly in FIG. 7). The screw 29 secures the plate 27 in place on the body 14 of the scalpel 10, so that the resiliently-biased detent means 13 is retained on the scalpel 10.

While the blade guard 11 is being slidably moved between its respective extended and retracted positions, the upper surface of the annular shoulder 23B slides along the bottom surface of the flanges 17 of the slot 16 under the upward biasing action of the spring 24. While doing this, the upper surface of the annular shoulder 23B presses against the flanges 17 until the detent pockets 19A or 19B become aligned therewith. When the detent pockets 19A and 19B become aligned with the shoulder 23B, the biasing action of the spring 24 urges the shoulder 23B upwardly into one of the detent pockets 19A or 19B and against the bottom surface of the retaining plate 27.

The force of the upper surface of the annular shoulder 23B coming into contact with the bottom surface of the retaining plate 27 produces a "click" which signals to the user of the scalpel 10 that the guard 11 has been removably locked into one of the selected retracted or extended positions thereof. In this respect, an auditory warning means or signal is provided for the user to make the user aware that the guard has been actually locked into the selected (retracted or extended) position without the necessity of having to visually observe the scalpel 10.

The guard 11 further has a closed-ended slot 30 formed therein extending substantially longitudinally along the guard 11 from the forward end to the rearward end thereof. This slot 30 may be formed in any suitable portion of the guard 11. However, it is contemplated herein that the slot 30 will be formed on one of the side walls of the guard 11.

Figure 8:
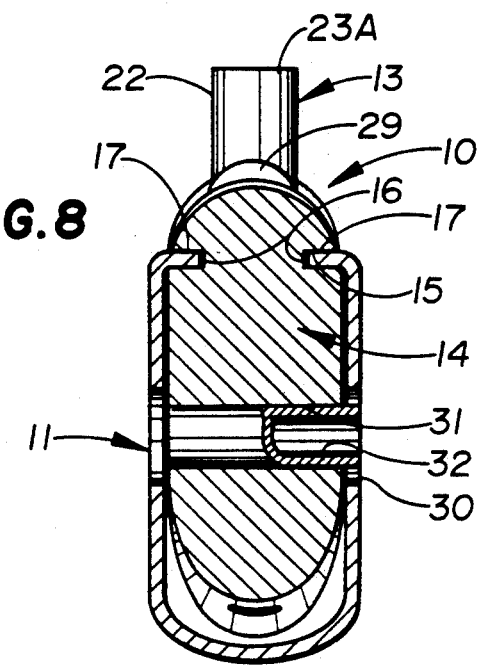
FIG. 8 is a cross-sectional view taken along lines 8—8 of FIG. 4 and drawn to an enlarged scale.

With further reference to FIG. 8, the body 14 of the scalpel 10 has a lateral bore 31 formed therein extending along an axis which is substantially perpendicular to the longitudinal axis of the body 14 of the scalpel 10. Disposed in the lateral bore 31, so as to extend outwardly therefrom, is a stop pin 32. The stop pin 32 is press-fitted or otherwise suitably secured in the bore 31. The stop pin 32 is thus carried by the body 14 of the scalpel 10, extends outwardly therefrom, and is received in the slot 30, such that the longitudinal sliding movement of the guard 11 is restricted so as to prevent the guard 11 from being slidably moved beyond its extended and retracted positions.

With reference to FIGS. 13A-13D and 14A-14D, the inherent utility and simplicity of the present invention is clearly illustrated. The surgeon, nurse, assistant or other health care provider can easily release the detent means 13 and manually slide the guard 11 rearwardly to its retracted position to expose the blade on the scalpel. Thereafter, the detent means 13 may again be released and the guard 11 may be easily advanced into its normal extended position to completely cover the blade 12 and prevent accidental or inadvertent cuts or nicks while transferring the scalpel 10 from the nurse to the surgeon, and vice versa, during a surgical procedure in an operating room or similar environment.

In an operating room environment, the tensions and pressures are intense, seconds count, and a life is often at stake. The surgeon, nurse or assistant must concentrate closely, cannot be distracted, and must keep his or her eyes on the patient and the medical equipment and instrumentation. Any concern with cuts or nicks incurred while transferring the scalpel from the nurse to the surgeon, and vice versa, is counter-productive and an unnecessary distraction. This distraction is especially pronounced when the patient is an AIDS carrier or a known HIV-positive patient.

Accordingly, the improved scalpel of the present invention greatly alleviates this potentially hazardous situation, allows the operating room personnel including the surgeon to concentrate solely on the patient and the instrumentation, and avoids the risk of becoming HIV or HBV infected by blood or body secretions from an inadvertent cut while a scalpel is being transferred.

Figure 15:
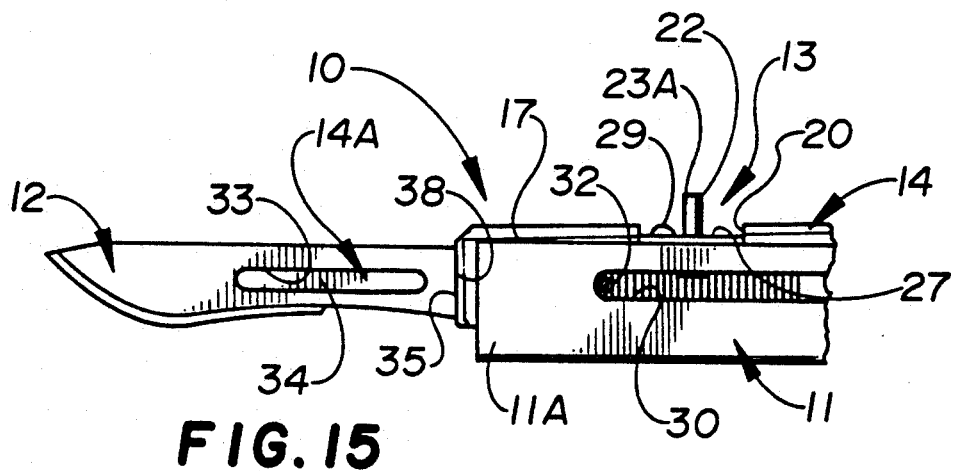
FIG. 15 is a side elevational view of an improved blade mounted on the scalpel of the present invention.
Figure 16:
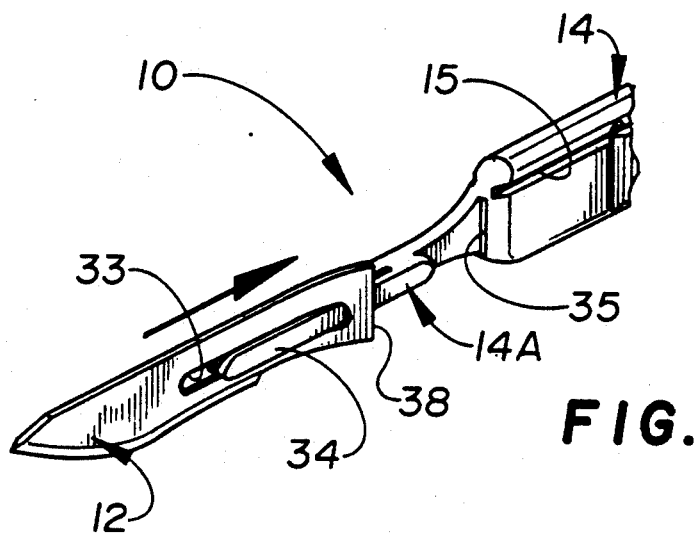
FIG. 16 is a partial exploded view, corresponding substantially to FIG. 15, but showing the manner in which the improved blade is mounted on the scalpel of the present invention.
Figure 17:
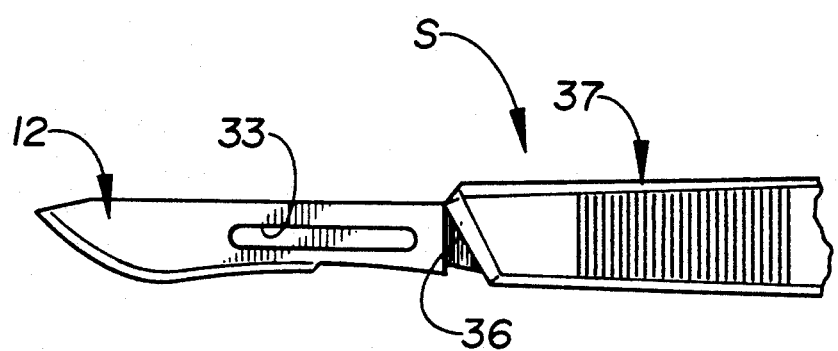
FIG. 17 is a side elevation view of the improved blade of the present invention mounted on a conventional (non-guarded) surgical scalpel.

With reference to FIGS. 15-17, the blade 12 has a closed slot 33 which fits over a laterally-extending longitudinal rib or projection 34 formed on the forward end 14a of the scalpel body 14, thereby removably mounting the blade 12 to the scalpel 10.

In a preferred embodiment, as shown more clearly in FIGS. 15 and 16, the forward end 14A of the scalpel body 14 has a shoulder 35 substantially at right angles thereto. This shoulder 35 corresponds to an angled shoulder 36 on a conventional non-guarded scalpel 37 as shown in FIG. 17. The angled shoulder 36 cooperates with a conventional blade (not shown) having a rearward angled portion complementary to the angled shoulder 36.

The improved blade 12 of the present invention has a rearward shoulder or edge 38 which is substantially at right angles thereto (as shown more clearly in FIG. 16) and complementary to the right angle shoulder 35 on the improved scalpel 10. Thus the improved blade 12 fits snugly against the shoulder 35 when the blade 12 is removably mounted on the scalpel 10.

The conventional scalpel blades (not shown) cannot be fitted to the improved scalpel 10 of the present invention. However, and as shown more clearly in FIG. 17, the improved blade 12 of the present invention can be fitted to a conventional non-guarded scalpel 37, if desired, as well as to the improved scalpel 10 of the present invention.

Obviously, many modifications may be made without departing from the basic spirit of the present invention. For example, if desired, the releasable spring-loaded detent pin could be carried by the sliding guard instead of the scalpel body. Accordingly, it will be appreciated by those skilled in the art that within the scope of the appended claims, the invention may be practiced other than has been specifically described herein.

What is claimed is:

1. A surgical scalpel, comprised of:
   the scalpel including a body having a rear portion and a forward portion;
   a surgical cutting blade;
   a surgical cutting blade attachment projection for receiving the surgical cutting blade thereon, the cutting blade attachment projection being integrally formed on the forward portion of the body of the scalpel and extending forwardly therefrom, so that the cutting blade thereon extends forwardly therefrom;
   a cutting blade guard carried by the body of the scalpel for selective longitudinal sliding movement of the guard on the body between an extended position, wherein the guard extends over the cutting blade, thereby selectively covering the cutting blade and protecting the user thereof, and a retracted position, wherein the guard is rearward of the cutting blade, thereby selectively exposing the cutting blade and permitting the use thereof; and
   a resiliently-biased detent means formed between the body of the scalpel and the blade guard for removably securing the blade guard in the respective extended and retracted positions thereof wherein the resilient-biased means includes:
   the cutting blade guard having at least one pair of locking detents formed therein, one of the locking detents of said pair being formed in a forward portion of the cutting blade guard, and the other of the locking detents of said pair being formed in a rearward portion of the cutting blade guard; and
   a resiliently-biased means carried by the body of the scalpel for selectively mating with one of the respective locking detents of the pair of locking detents formed in the blade guard when the blade guard is disposed in the respective extended and retracted positions thereof, whereby the mating of the locking means with the one of the locking detents formed in the forward portion of the blade guard removably secures the blade guard in the respective retracted position thereof, and further whereby the mating of the locking means with the one of the locking detents formed in the rearward portion of the blade guard removably secures the blade guard in the respective extended position thereof.

2. The surgical scalpel of claim 1, wherein the resiliently-biased means includes a locking pin carried by the body of the scalpel, the locking pin being constantly resiliently-biased outwardly and into the locking detents.

3. The surgical scalpel of claim 2, wherein the resiliently-biased means further includes:
   the locking pin having an annular shoulder for being received in the locking detents; and
   a biasing spring disposed between the body of the scalpel and the annular shoulder of the locking pin, so as to abut the body of the scalpel and the annular shoulder of the locking pin for constantly resiliently-biasing the annular shoulder of the locking pin outwardly and into the respective locking detents.

4. The surgical scalpel of claim 3, wherein the locking pin further includes a release extension adjacent to the annular shoulder and extending outwardly therefrom, so that the release extension may be pushed downwardly for overcoming the resilient biasing action of the biasing spring, whereby the blade guard is released for permitting the sliding movement of the blade guard on the body of the scalpel between the extended and retracted positions.

5. The surgical scalpel of claim 4 wherein the release extension has an enlarged rounded end formed thereon, thereby facilitating the pushing of the locking pin against the biasing spring for overcoming the biasing action of the biasing spring for disengaging the upper abutment end of the locking pin from the locking detent, so that the blade guard may be selectively moved between the first and the second positions thereof.

6. The surgical scalpel of claim 3, wherein the resiliently-biased means further includes:
   the locking pin further having a lower stem adjacent to the shoulder and extending therefrom;
   the biasing spring received around the stem of the locking pin, the spring having one end abutting the body of the scalpel and a second end abutting the shoulder, whereby the constant resiliently-biasing effect is exerted on the pin.

7. The surgical scalpel of claim 1, further comprised of:
   the resiliently-biased means including a locking pin carried by the body of the scalpel, the locking pin being constantly resiliently-biased outwardly and into the locking detents;
   the locking pin including a release extension and an annular shoulder formed adjacent to the release extension;
   the cutting blade guard having a longitudinal slot formed therein, the longitudinal slot having a width being greater than the release extension of the locking pin, so as to receive the release extension of the locking pin therein, and less than the annular shoulder of the locking pin; and
   the longitudinal slot including a pair of enlarged portions formed therein, one of said enlarged portions being formed in the forward portion of the cutting blade guard and the other of the said enlarged portions being formed in the rearward portion of the cutting blade guard, whereby the locking detents are defined in the cutting blade guard for receiving the annular shoulder of the locking pin therein, so that the cutting blade guard is locked into, respectively, extended position and the retracted position thereof.

8. The surgical scalpel of claim 7, further comprised of:
   the cutting blade guard having a respective edges defined on each side of the longitudinal slot that is formed therein;
   a guide flange formed on at least a portion of each of the respective edges of the cutting blade guard, each of said flanges formed so as to be oriented towards the body of the scalpel;
   the body of the scalpel having a pair of guide tracks formed therein such that each guide track receives one of the respective guide flanges therein, whereby the selective sliding longitudinal movement of the cutting blade guard on the body of the scalpel is facilitated.

9. The surgical scalpel of claim 1, wherein the resiliently-biased means includes a ball-spring detent.

10. The surgical scalpel of claim 1, further comprised of:
    the cutting blade guard having a closed-ended stop slot formed therein, said stop slot extending substantially longitudinally along the guard from the forward end to the rearward end thereof; and
    a stop pin carried by the body of the scalpel and extending outwardly therefrom, so as to be received in the stop slot, whereby the longitudinal sliding movement is restricted so as to prevent the guard from being sliding moved beyond the extended and retracted positions thereof.

11. A surgical scalpel, comprised of:
    the scalpel including a body having a rear portion and a forward portion;
    a surgical cutting blade;
    a surgical cutting blade attachment projection for receiving the surgical cutting blade thereon, the cutting blade attachment projection being integrally formed on the forward portion of the body of the scalpel and extending forwardly therefrom, so that the cutting blade thereon extends forwardly therefrom;
    a cutting blade guard carried by the body of the scalpel for selective longitudinal sliding movement of the guard on the body between a forward position, wherein the guard extends over the cutting blade, thereby selectively covering the cutting blade and protecting the user thereof, and a rearward position, wherein the guard is rearward of the cutting blade, thereby selectively exposing the cutting blade and permitting the use thereof;
    the cutting blade guard having at least one pair of locking detents formed therein, one of the locking detents of said pair being formed in a forward portion of the cutting blade guard, and the other of the locking detents of said pair being formed in a rearward portion of the cutting blade guard;
    a locking pin carried by the body of the scalpel, the locking pin having an release extension, an annular shoulder for being received in the locking detents, and a lower stem adjacent to the shoulder and extending therefrom oppositely the release extension;
    a biasing spring received around the stem of the locking pin, the spring having one end abutting the body of the scalpel and a second end abutting the annular shoulder of the locking pin, whereby the constant resiliently-biasing effect is exerted on the pin, so as to abut the body of the scalpel and the annular shoulder of the locking pin for constantly resiliently-biasing the locking pin outwardly, such that the annular shoulder thereof is received in the locking detents for selectively mating with one of the respective locking detents of the pair of locking detents formed in the blade guard when the blade guard is disposed in the respective forward and rearward positions thereof, whereby the mating of the annular shoulder of the locking pin with the one of the locking detents formed in the forward portion of the blade guard removably secures the blade guard in the respective rearward position thereof, and further whereby the mating of the annular shoulder of the locking pin with the one of the locking detents formed in the rearward portion of the blade guard removably secures the blade guard in the respective forward position thereof; and the release extension of the locking pin having an enlarged rounded end formed thereon, thereby facilitating the pushing of the locking pin against the biasing spring for overcoming the biasing action of the biasing spring for disengaging the annular shoulder of the locking pin from the locking detent, so that the blade guard may be selectively moved between the forward and the rearward positions thereof.

12. A surgical scalpel, comprised of:

the scalpel including a body having a rear portion and a forward portion;

a surgical cutting blade;

a surgical cutting blade attachment projection for receiving the surgical cutting blade thereon, the cutting blade attachment projection being integrally formed on the forward portion of the body of the scalpel and extending forwardly therefrom, so that the cutting blade thereon extends forwardly therefrom;

a cutting blade guard carried by the body of the scalpel for selective longitudinal sliding movement of the guard on the body between a forward position, wherein the guard extends over the cutting blade, thereby selectively covering the cutting blade and protecting the user thereof, and a rearward position, wherein the guard is rearward of the cutting blade, thereby selectively exposing the cutting blade and permitting the use thereof;

the cutting blade guard having at least one pair of locking detents formed therein, one of the locking detents of said pair being formed in a forward portion of the cutting blade guard, and the other of the locking detents of said pair being formed in a rearward portion of the cutting blade guard;

a locking pin carried by the body of the scalpel, the locking pin including a release extension and an annular shoulder formed adjacent to the release extension, the locking pin being constantly resiliently-biased outwardly, such that the annular shoulder is received in the respective locking detents for selectively mating with one of the respective locking detents of the pair of locking detents formed in the blade guard when the blade guard is disposed in the respective forward and rearward positions thereof, whereby the mating of the annular shoulder of the locking pin with the one of the locking detents formed in the forward portion of the blade guard removably secures the blade guard in the respective rearward position thereof, and further whereby the mating of the annular shoulder of the locking pin with the one of the locking detents formed in the rearward portion of the blade guard removably secures the blade guard in the respective forward position thereof;

the cutting blade guard having a longitudinal slot formed therein, the longitudinal slot having a width being greater than the release extension and the annular shoulder of the locking pin, so as to receive the release extension and the annular shoulder of the locking pin therethrough; and the longitudinal slot including a pair of enlarged portions formed therein, one of said enlarged portions being formed in the forward portion of the cutting blade guard and the other of the said enlarged portions being formed in the rearward portion of the cutting blade guard, whereby the locking detents are defined in the cutting blade guard for receiving the annular shoulder of the locking pin therein, so that the cutting blade guard is locked into, respectively, forward position and the rearward position thereof.

13. A cutting blade guard for a surgical scalpel of the type having a body and a surgical cutting blade carried by the body of the scalpel, the cutting blade guard comprised of:

the cutting blade guard including a body carried by the body of the scalpel for selective longitudinal sliding movement of the guard on the body of the scalpel between a forward position, wherein the guard extends over the cutting blade, thereby selectively covering the cutting blade and protecting the user thereof, and a rearward position, wherein the guard is rearward of the cutting blade, thereby selectively exposing the cutting blade and permitting the use thereof; and the body of the cutting blade guard having a forward portion and a rearward portion, the body of the cutting blade guard further having at least one pair of locking detents formed therein, one of the locking detents of said pair being formed in a forward portion of the cutting blade guard, and the other of the locking detents of said pair being formed in a rearward portion of the cutting blade guard;

whereby a resiliently-biased locking means carried by the body of the scalpel may selectively mate with one of the respective locking detents of the pair of locking detents formed in the cutting blade guard when the cutting blade guard is disposed in the respective forward and rearward positions thereof, whereby the mating of the locking means with the one of the locking detents formed in the forward portion of the cutting blade guard removably secures the cutting blade guard in the respective rearward position thereof, and further whereby the mating of the locking means with the one of the locking detents formed in the rearward portion of the cutting blade guard removably secures the cutting blade guard in the respective forward position thereof.

14. The cutting blade guard of claim 13, further comprised of:

the body of the cutting blade guard having a longitudinal slot formed therein;

the longitudinal slot including a pair of enlarged portions formed therein, one of said enlarged portions being formed in the forward portion of the cutting blade guard and the other of the said enlarged portions being formed in the rearward portion of the cutting blade guard, whereby the locking detents are defined in the cutting blade guard for removably receiving therein the constantly resiliently-biased locking means, so that the cutting blade guard may be selectively locked into, respectively, forward position and the rearward position thereof.

15. The cutting blade guard of claim 14, wherein the body of the scalpel further having a pair of guide tracks formed therein, the cutting blade guard further comprised of:

the cutting blade guard having a respective edges defined on each side of the longitudinal slot that is formed therein; and a guide flange formed on at least a portion of each of the respective edges of the cutting blade guard, each of said flanges formed so as to be oriented towards the body of the scalpel;

whereby each of the guide flanges is received in a respective guide track, so that selective sliding longitudinal movement of the cutting blade guard on the body of the scalpel is facilitated.

16. The cutting blade guard of claim 13, wherein the body of the scalpel further having a stop pin carried thereby so as to extend outwardly therefrom, the cutting blade guard further comprised of:

the cutting blade guard having a closed-ended stop slot formed therein, said stop slot extending substantially longitudinally along the guard from the forward end to the rearward end thereof, whereby the stop pin carried by the body of the scalpel is received in the stop slot, so that the longitudinal sliding movement is restricted to prevent the guard from being sliding moved beyond the first and second positions thereof.

17. In combination, a surgical scalpel, a surgical cutting blade therefore and a surgical cutting blade guard, the combination comprised of:

the scalpel including a body having a rear portion and a forward portion;

a surgical cutting blade attachment projection for receiving the surgical cutting blade thereon, the cutting blade attachment projection being integrally formed on the forward portion of the body of the scalpel and extending forwardly therefrom, so that the cutting blade thereon extends forwardly therefrom;

the cutting blade including a blade body having a forward end and a rearward end; and the body of the cutting blade having an attachment aperture formed therein, whereby the attachment projection of the scalpel may be removably received in the attachment aperture formed in the body of the cutting blade;

the attachment aperture formed in the cutting blade having a width and a length, the width of the attachment aperture being substantially the same along the entire length thereof;

a cutting blade guard carried by the body of the scalpel for selective longitudinal sliding movement of the guard on the body between a forward position, wherein the guard extends over the cutting blade, thereby selectively covering the cutting blade and protecting the user thereof, and a rearward position, wherein the guard is rearward of the cutting blade, thereby selectively exposing the cutting blade and permitting the use thereof; wherein the guard comprises a U-shaped member closely approximating the external contours of the scalpel, and a resiliently-biased locking detent means formed between the body of the scalpel and the blade guard for removably securing the blade guard in the respective forward and rearward positions thereof, wherein the scalpel body has a top portion, a bottom portion, and a relatively-thin width, thereby defining a longitudinal vertical center plane for the scalpel body, and wherein the resiliently-biased locking detent means includes a detent member having a first portion slidably guided within the scalpel body, disposed within the longitudinal vertical center plane thereof, the having a second portion projecting above the top portion of the scalpel body for convenient manual manipulation.

18. In combination, a surgical scalpel, a surgical cutting blade therefore and a surgical cutting blade guard, the combination comprised of:

the scalpel including a body having a rear portion and a forward portion;

a surgical cutting blade attachment projection for receiving the surgical cutting blade thereon, the cutting blade attachment projection being integrally formed on the forward portion of the body of the scalpel and extending forwardly therefrom, so that the cutting blade thereon extends forwardly therefrom;

the cutting blade including a blade body having a forward end and a rearward end;

a cutting blade formed on the forward end of the cutting blade body; and the body of the cutting blade having a attachment aperture formed therein, whereby the attachment projection of the scalpel may be removably received in the attachment aperture formed in the body of the cutting blade;

the attachment aperture formed in the cutting blade having a width and a length, the width of the attachment apertures being substantially the same along the entire length thereof;

a cutting blade guard carried by the body of the scalpel for selective longitudinal sliding movement of the guard on the body between a forward position, wherein the guard extends over the cutting blade, thereby selectively covering the cutting blade and protecting the user thereof, and a rearward position, wherein the guard is rearward of the cutting blade, thereby selectively exposing the cutting blade and permitting the use thereof;

the cutting blade guard having at least one pair of locking detents formed therein, one of the locking detents of said pair being formed in a forward portion of the cutting blade guard, and the other of the locking detents of said pair being formed in a rearward portion of the cutting blade guard;

a locking pin carried by the body of the scalpel, the locking pin having an annular shoulder formed thereon for being received in the locking detents, and a lower stem adjacent to the shoulder and extending therefrom;

a biasing spring received around the stem of the locking pin, the spring having one end abutting the body of the scalpel and a second end abutting the annular shoulder of the locking pin, whereby the constant resiliently-biasing effect is exerted on the pin, so as to abut the body of the scalpel and the annular shoulder of the locking pin for constantly resiliently-biasing the locking pin outwardly and into the locking detents for selectively mating with one of the respective locking detents of the pair of locking detents formed in the blade guard when the blade guard is disposed in the respective forward and rearward positions thereof, whereby the mating of the locking pin with the one of the locking detents formed in the forward portion of the blade guard removably secures the blade guard in the respective rearward position thereof, and further whereby the mating of the locking pin with the one of the locking detents formed in the rearward portion of the blade guard removably secures the blade guard in the respective forward position thereof; and the locking pin further having a release extension formed thereon adjacent to the annular shoulder, so as to extend therefrom oppositely from the lower stem, the release extension of the locking pin having an enlarged rounded end formed thereon, thereby facilitating the pushing of the locking pin against the biasing spring for overcoming the biasing action of the biasing spring for disengaging the annular shoulder of the locking pin from the locking detent, so that the blade guard may be selectively moved between the forward and the rearward positions thereof.

19. In combination, a surgical scalpel, a surgical cutting blade therefor and a surgical cutting blade guard, the combination comprised of:

the scalpel including a body having a rear portion and a forward portion;

a surgical cutting blade attachment projection for receiving the surgical cutting blade thereon, the cutting blade attachment projection being integrally formed on the forward portion of the body of the scalpel and extending forwardly therefrom, so that the cutting blade thereon extends forwardly therefrom;

the cutting blade including a blade body having a forward end and a rearward end;

a cutting blade formed on the forward end of the cutting blade body; and the body of the cutting blade having a attachment aperture formed therein, whereby the attachment projection of the scalpel may be removably received in the attachment aperture formed in the body of the cutting blade;

the attachment aperture formed in the cutting blade having a width and a length, the width of the attachment apertures being substantially the same along the entire length thereof;

a cutting blade guard carried by the body of the scalpel for selective longitudinal sliding movement of the guard on the body between a forward position, wherein the guard extends over the cutting blade, thereby selectively covering the cutting blade and protecting the user thereof, and a rearward position, wherein the guard is rearward of the cutting blade, thereby selectively exposing the cutting blade and permitting the use thereof;

the cutting blade guard having at least one pair of locking detents formed therein, one of the locking detents of said pair being formed in a forward portion of the cutting blade guard, and the other of the locking detents of said pair being formed in a rearward portion of the cutting blade guard;

a locking pin carried by the body of the scalpel, the locking pin including a release extension, and an annular shoulder formed adjacent to the release extension, the locking pin being constantly resiliently-biased outwardly and into the locking detents for selectively mating with one of the respective locking detents of the pair of locking detents formed in the blade guard when the blade guard is disposed in the respective forward and rearward positions thereof, whereby the mating of the locking pin with the one of the locking detents formed in the forward portion of the blade guard removably secures the blade guard in the respective rearward position thereof, and further whereby the mating of the locking pin with the one of the locking detents formed in the rearward portion of the blade guard removably secures the blade guard in the respective forward position thereof;

the cutting blade guard having a longitudinal slot formed therein, the longitudinal slot having a width being greater than the release extension and the annular shoulder of the locking pin, so as to receive the release extension and the annular shoulder of the locking pin therein, and less than the annular shoulder of the locking pin; and the longitudinal slot including a pair of enlarged portions formed therein, one of said enlarged portions being formed in the forward portion of the cutting blade guard and the other of the said enlarged portions being formed in the rearward portion of the cutting blade guard, whereby the locking detents are defined in the cutting blade guard for receiving the annular shoulder of the locking pin therein, so that the cutting blade guard is locked into, respectively, forward position and the rearward position thereof.

20. A guard for the blade of a surgical scalpel, wherein the scalpel has a main body portion including a forward section upon which the blade is removably mounted, comprising a substantially U-shaped channel including a pair of parallel side walls connected by a bottom wall, such that the guard closely straddles the main body portion of the scalpel and does not interfere with the normal use of the scalpel during a procedure performed in an operating room, means for slidably mounting the guard on the body of the scalpel for limited movement longitudinally of the body of the scalpel to thereby define a first extended position covering the blade and a second retracted position exposing the blade, such that the surgeon, nurse or assistant in the operating room may move the guard from one position to another in a one-handed movement without taking his or her eyes away from the patient, and the blade guard providing a tactile indication of the respective position of the guard on the body of the scalpel, so that either the surgeon or the nurse in the operating room does to have to takehis or her eyes away from the patient while passing the scalpel from one to another during the operating procedure, but rather will know instinctively from the feel of the scalpel itself, thereby preventing the usual cuts or nicks normally encountered in passing a surgical scalpel from the assistant to the surgeon and vice versa during an operating procedure, and thereby substantially reducing the risk of the surgeon, nurse or assistant inadvertently acquiring an infectious disease, such as HIV or HBV, in the operating room or similar medical environment, wherein the scalpel body has a top portion, a bottom portion, and a relatively-thin width, thereby defining a longitudinal vertical center plane for the scalpel body, and wherein a detent means is provided between the guard and the scalpel body, the detent means including a resiliently-biased detent member having a first portion slidably guided within the scalpel body, disposed within the longitudinal vertical center plane thereof, and having a second portion projecting above the top portion of the scalpel body for convenient manual manipulation.

21. A guard for the blade of a surgical scalpel, wherein the scalpel has a main body portion including a forward section upon which the blade is removably mounted, comprising a substantially U-shaped channel including a pair of parallel side walls connected by a bottom wall, such that the guard closely straddles the main body portion of the scalpel and does not interfere with the normal use of the scalpel during a procedure performed in an operating room, means for slidably mounting the guard on the body of the scalpel for limited movement longitudinally of the body of the scalpel to thereby define a first extended position covering the blade and a second retracted position exposing the blade, such that the surgeon, nurse or assistant in the operating room may move the guard from one position to another in a one-handed movement without taking his or her eyes away from the patient, and the blade guard providing a tactile indication of the respective position of the guard on the body of the scalpel, so that either the surgeon or the nurse in the operating room does not have to take his or her eyes away from the patient while passing the scalpel from one to another during the operating procedure, but rather will know instinctively from the feel of the scalpel itself, thereby preventing the usual cuts or nicks normally encountered in passing a surgical scalpel from the assistant to the surgeon and vice versa during an operating procedure, and thereby substantially reducing the risk of the surgeon, nurse or assistant inadvertently acquiring an infectious disease, such as HIV or HBV, in the operating room or similar medical environment further including a pin carried by the scalpel body and projecting laterally therefrom, and one of the side walls of the guard having a closed slot formed therein for receiving the pin, thereby defining the respective extended and retracted positions of the guard.

22. A guard for the blade of a surgical scalpel, wherein the scalpel has a main body portion including a forward section upon which the blade is removably mounted, comprising a substantially U-shaped channel including a pair of parallel side walls connected by a bottom wall, such that the guard closely straddles the main body portion of the scalpel and does not interfere with the normal use of the scalpel during a procedure performed in an operating room, means for slidably mounting the guard on the body of the scalpel for limited movement longitudinally of the body of the scalpel to thereby define a first extended position covering the blade and a second retracted position exposing the blade, such that the surgeon, nurse or assistant in the operating room may move the guard from one position to another in a one-handed movement without taking his or her eyes away from the patient, and the blade guard providing a tactile indication of the respective position of the guard on the body of the scalpel, so that either the surgeon or the nurse in the operating room does not have to take his or her eyes away from the patient while passing the scalpel from one to another during the operating procedure, but rather will know instinctively from the feel of the scalpel itself, thereby preventing the usual cuts or nicks normally encountered in passing a surgical scalpel from the assistant to the surgeon and vice versa during an operating procedure, and thereby substantially reducing the risk of the surgeon, nurse or assistant inadvertently acquiring an infectious disease, such as HIV or HBV, in the operating room or similar medical environment, wherein the bottom wall of the guard has a cut-out portion formed therein to facilitate manual movement of the guard.

23. A guard for the blade of a surgical scalpel, wherein the scalpel has a main body portion including a forward section upon which the blade is removably mounted, comprising a substantially U-shaped channel including a pair of parallel side walls connected by a bottom wall, such that the guard closely straddles the main body portion of the scalpel and does not interfere with the normal use of the scalpel during a procedure performed in an operating room, means for slidably mounting the guard on the body the scalpel for limited movement longitudinally of the body of the scalpel to thereby define a first extended position covering the blade and a second retracted position exposing the blade, such that the surgeon, nurse or assistant in the operating room may move the guard from one position to another in a one-handed movement without taking his or her eyes away from the patient, and the blade guard providing a tactile indication of the respective position of the guard on the body of the scalpel, so that either the surgeon or the nurse in the operating room does not have to takehis or her eyes away from the patient while passing the scalpel from one to another during the operating procedure, but rather will known instinctively from the feel of the scalpel itself, thereby preventing the usual cuts or nicks normally encountered in passing a surgical scalpel from the assistant to the surgeon and vice versa during an operating procedure, and thereby substantially reducing the risk of the surgeon, nurse or assistant inadvertently acquiring an infectious disease, such as HIV or HVB, in the operating room or similar medical environment, further including releasable detented locking means forward between the guard and the body of the scalpel and operative in the first and second positions of the guard, respectively.

24. The guard of claim 23, wherein the releasable detented locking means comprises a spring-loaded manually-accessible detent pin carried by the scalpel body, and the guard having a pair of detent pockets to selectively receive the detent pin, such that the detent pin may be manually depressed to clear the respective detent pocket and allow the guard to be slidably moved.

25. The guard of claim 24, wherein each of the side walls of the guard has an inturned flange, and wherein the detent pockets are formed as respective cut-outs in the inturned flanges.

26. A guard for the blade of a surgical scalpel, wherein the scalpel has a main body portion including a forward section upon which the blade is removably mounted, comprising a substantially U-shaped channel including a pair of parallel side walls connected by a bottom wall, such that the guard closely straddles the main body portion of the scalpel and does not interfere with the normal use of the scalpel during a procedure performed in an operating room, mounting means for slidably mounting the guard on the body of the scalpel for limited movement longitudinally of the body of the scalpel, said mounting means including a pin carried by the scalpel body and projecting laterally therefrom, and one of the side walls of the U-shaped channel having a longitudinal closed slot formed therein and receiving the pin, thereby defining a first extended position covering the blade and a second retracted position exposing the blade, releasable detented locking means formed between the guard and the body of the scalpel and operative in the first and second positions of the guard, respectively, such that the surgeon, nurse or assistant in the operating room may move the guard from one position to another in a one-handed movement without taking his or her eyes off of the patient, the releasable detented locking means comprising a spring-loaded manually-accessible detent pin carried by the scalpel body, and the guard having a pair of detent pockets to selectively receive the detent pin, such that the detent pin may be manually depressed to clear the respective detent pocket and allow the guard to be slidably moved, the side walls of the guard each having an inturned flange, and the detent pockets comprising respective longitudinally-spaced respective openings formed in the inturned flanges of the side walls of the guard, the bottom wall of the guard having a thumb cut-out portion formed therein to facilitate the limited longitudinal sliding movement of the guard upon release of the detent means, and wherein the blade guard provides a tactile indication of the respective position of the guard on the body of the scalpel, so that either the surgeon or the nurse in the operating room does not have to take his or her eyes away from the patient while passing the scalpel form one to another during the operating procedure, but rather will know instinctively from the feel of the scalpel itself, thereby preventing the usual cuts or nicks normally encountered in passing a surgical scalpel from the assistant to the surgeon and vice versa during an operating procedure, and thereby substantially reducing the risk of the surgeon, nurse or assistant inadvertently acquiring an infectious disease, such as the HIV virus, in the operating room or similar medical environment.

27. In combination, a blade for a surgical scalpel, wherein the scalpel has a body including a forward portion provided with a right-angularly disposed shoulder, the blade having a rearward right-angularly disposed edge complementary to, and bearing against, the shoulder on the scalpel body, such that the blade is snugly received on the forward portion of the scalpel body, means for detachably mounting the blade on the scalpel, a manually-movable U-shaped guard means carried by the body of the scalpel and closely approximating the external contours of the scalpel body for selectively covering and exposing the blade, all in a one-handed operation without looking at the scalpel, wherein the scalpel body has a top portion, a bottom portion, and a relatively-thin width, thereby defining a longitudinal vertical center plane for the scalpel body, and wherein a detent means is provided between the guard and the scalpel body, the detent means including a resiliently-biased detent member having a first portion slidably guided within the scalpel body, disposed within the longitudinal vertical center plane thereof, and having a second portion projecting above the top portion of the scalpel body for convenient manual manipulation.

28. In a guarded scalpel for surgical use, wherein the guarded scalpel includes a relatively-thin handle having a top portion and further having respective side portions defining therebetween a vertical longitudinal center plane, a blade mounted on the handle, and a guard closely mounted on the handle for sliding movement thereon about a longitudinal axis and from an advanced position in which the blade is covered to a retracted position in which the blade is exposed, the improvement comprising a two-position detent means between the guard and the handle and including a resiliently-biased detent member having a first portion slidably guided within the handle substantially along the vertical longitudinal center plane for limited movement with respect to the handle about an axis which is perpendicular to the longitudinal axis of the guard, the detent member having a second portion projecting above the handle for manual manipulation, thereby maintaining the relatively-thin external contours of the guarded scalpel, and detent pocket means formed on the guard, longitudinally spaced apart thereon, and cooperating with the projecting second portion of the detent member to define the respective advanced and retracted positions of the guard.

29. In a guarded scalpel for surgical use, wherein the guarded scalpel includes a handle having a top portion, a bottom portion, and respective side portions defining therebetween a vertical longitudinal center plane therebetween, and wherein a guard is slidably mounted on the handle, the guard having an advanced position in which a blade on the handle is covered and further having a retracted position in which the blade is exposed, the improvement comprising a two-position detent means carried by the handle, disposed substantially in the longitudinal vertical center plane of the handle, and operative between the guard and the handle, the detent means including a first manually-manipulatable actuating means projecting above the top portion of the handle, and the guard including a second manually-manipulatable means on the bottom portion thereof for sliding the guard, the first and second manually-manipulatable means having a different tactile feel, whereby, as the guarded scalpel is passed from one health care provider to another in an operating room, the other health care provided receiving the guarded scalpel will known intuitively the orientation of the guarded scalpel as well as the position of the guard without actually looking at the guarded scalpel.

* * * * *